United States Patent
Hyuugaji

(10) Patent No.: US 10,774,165 B2
(45) Date of Patent: *Sep. 15, 2020

(54) POLYMER COMPOSITION, ARTICLE, MEDICAL DEVICE, ARTICLE PRODUCTION METHOD, AND CELL CLUSTER PRODUCTION METHOD

(71) Applicants: JSR CORPORATION, Minato-ku (JP); JSR LIFE SCIENCES CORPORATION, Minato-ku (JP)

(72) Inventor: Satoshi Hyuugaji, Minato-ku (JP)

(73) Assignees: JSR CORPORATION, Minato-ku (JP); JSR LIFE SCIENCES CORPORATION, Minato-ku (JP)

(*) Notice: Subject to any disclaimer, the term of this patent is extended or adjusted under 35 U.S.C. 154(b) by 87 days.

This patent is subject to a terminal disclaimer.

(21) Appl. No.: 15/749,542

(22) PCT Filed: Aug. 4, 2016

(86) PCT No.: PCT/JP2016/072894
§ 371 (c)(1),
(2) Date: Feb. 1, 2018

(87) PCT Pub. No.: WO2017/022815
PCT Pub. Date: Feb. 9, 2017

(65) Prior Publication Data
US 2018/0223024 A1   Aug. 9, 2018

(30) Foreign Application Priority Data

Aug. 4, 2015 (JP) .................. 2015-154293
Aug. 11, 2015 (JP) .................. 2015-159094
Aug. 11, 2015 (JP) .................. 2015-159095

(51) Int. Cl.
| | |
|---|---|
| C08L 83/04 | (2006.01) |
| C09D 133/14 | (2006.01) |
| C08F 220/34 | (2006.01) |
| C08F 220/20 | (2006.01) |
| C08F 226/10 | (2006.01) |
| C08F 220/54 | (2006.01) |
| C08F 220/36 | (2006.01) |
| C09D 4/00 | (2006.01) |
| A61L 27/34 | (2006.01) |
| A61L 27/50 | (2006.01) |
| A61L 29/14 | (2006.01) |
| A61L 29/10 | (2006.01) |
| A61L 31/10 | (2006.01) |
| C09D 133/26 | (2006.01) |
| A61L 31/14 | (2006.01) |
| A61L 17/14 | (2006.01) |
| C08F 216/12 | (2006.01) |
| C08F 220/28 | (2006.01) |
| C08F 299/08 | (2006.01) |
| A61L 27/16 | (2006.01) |

(Continued)

(52) U.S. Cl.
CPC .......... *C08F 220/34* (2013.01); *A61L 17/145* (2013.01); *A61L 27/34* (2013.01); *A61L 27/50* (2013.01); *A61L 29/10* (2013.01); *A61L 29/14* (2013.01); *A61L 31/10* (2013.01); *A61L 31/14* (2013.01); *C08F 216/12* (2013.01); *C08F 220/20* (2013.01); *C08F 220/28* (2013.01); *C08F 220/36* (2013.01); *C08F 220/54* (2013.01); *C08F 226/10* (2013.01); *C08F 299/08* (2013.01); *C09D 4/00* (2013.01); *C09D 133/26* (2013.01); *A61L 27/16* (2013.01); *A61L 29/041* (2013.01); *A61L 2400/10* (2013.01); *C08L 83/04* (2013.01); *C09D 133/14* (2013.01); *C12N 5/0018* (2013.01)

(58) Field of Classification Search
None
See application file for complete search history.

(56) References Cited

U.S. PATENT DOCUMENTS

| 6,020,071 A | 2/2000 | Watson |
| 6,281,319 B1 | 8/2001 | Mentak |

(Continued)

FOREIGN PATENT DOCUMENTS

| JP | 5-168695 A | 7/1993 |
| JP | 2890316 B2 | 5/1999 |

(Continued)

OTHER PUBLICATIONS

International Search Report dated Nov. 8, 2016 in PCT/JP2016/072894, 2 pages.

Ruth A. Roberts, et al. "Hepatocyte Spheroids: Prolonged Hepatocyte Viability for in Vitro Modeling of Nongenotoxic Carcinogenesis", Fundamental and Applied Toxicology, vol. 21, No. 2, 1993, pp. 149-158.

(Continued)

Primary Examiner — Richard A Huhn
(74) Attorney, Agent, or Firm — Oblon, McClelland, Maier & Neustadt, L.L.P.

(57) ABSTRACT

The present invention relates to: a polymer composition; an article; a medical device; an article production method; and a cell cluster production method. The polymer composition contains a polymer having the following repeating units (A) and (B) and is one selected from the group consisting of a medical device composition, a cell adhesion inhibitor, and a silicone substrate treatment composition:

(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

10 Claims, No Drawings

(51) Int. Cl.
*A61L 29/04* (2006.01)
*C12N 5/00* (2006.01)

(56) References Cited

U.S. PATENT DOCUMENTS

| | | |
|---|---|---|
| 2001/0056165 A1 | 12/2001 | Mentak |
| 2002/0007032 A1 | 1/2002 | Mentak |
| 2002/0128417 A1* | 9/2002 | Mentak .................. A61L 27/16 526/318.1 |
| 2004/0052746 A1 | 3/2004 | Tamareselvy et al. |
| 2004/0241130 A1* | 12/2004 | Tamareselvy ............ A61K 8/04 424/70.16 |
| 2007/0010883 A1 | 1/2007 | Mentak |
| 2008/0014160 A1 | 1/2008 | Faivre et al. |
| 2008/0233069 A1 | 9/2008 | Tamareselvy et al. |
| 2010/0056647 A1 | 3/2010 | Graham et al. |
| 2016/0115435 A1 | 4/2016 | Otani et al. |
| 2016/0122576 A1 | 5/2016 | Hiroi et al. |
| 2016/0129176 A1 | 5/2016 | Kanaki et al. |
| 2016/0338939 A1 | 11/2016 | Graham et al. |
| 2017/0058237 A1* | 3/2017 | Iso ....................... C11D 3/3765 |
| 2018/0217294 A1* | 8/2018 | Hyuugaji ............... C08F 220/36 |
| 2018/0356561 A1* | 12/2018 | Hyugaji .................... C08F 2/44 |

FOREIGN PATENT DOCUMENTS

| | | |
|---|---|---|
| JP | 11-506375 A | 6/1999 |
| JP | 3131950 B2 | 2/2001 |
| JP | 2001-252896 A | 9/2001 |
| JP | 2002-542317 A | 12/2002 |
| JP | 3443891 B2 | 9/2003 |
| JP | 2005-125280 A | 5/2005 |
| JP | 2006-512425 A | 4/2006 |
| JP | 2008-82961 A | 4/2008 |
| JP | 2008-185423 A | 8/2008 |
| JP | 2012-501311 A | 1/2012 |
| WO | WO 2014/196652 A1 | 12/2014 |

OTHER PUBLICATIONS

Office Action dated Mar. 3, 2020 in corresponding Japanese Patent Application No. 2017-533116 (with English Translation), 7 pages.

* cited by examiner

POLYMER COMPOSITION, ARTICLE, MEDICAL DEVICE, ARTICLE PRODUCTION METHOD, AND CELL CLUSTER PRODUCTION METHOD

TECHNICAL FIELD

The present invention (I) relates to: a medical device composition; a medical device; and a method of producing the same. Particularly, the present invention (I) relates to: a medical device composition capable of imparting excellent lubricity to the surface of a medical device; a medical device having a lubricant surface; and a method of producing the medical device.

The present invention (II) relates to: a cell adhesion inhibitor; a cell culture equipment; a method of producing the equipment; and a method of producing a cell cluster.

The present invention (III) relates to: a silicone substrate treatment composition; a silicone substrate; a silicone substrate having a microchannel; and a method of producing a silicone substrate.

BACKGROUND ART (I) In the medical field, medical devices that include a part coming into contact with a living body, such as catheters, tubes, endoscopes and insertion tools, are required to have a lubricant surface for inhibiting damage to a living body and deterioration of an apparatus that are caused by friction due to contact and for improving the operability. However, conventional surfaces generally exhibit low lubricity upon coming into contact with a biological tissue or the like and have poor hydrophilicity; therefore, such conventional surfaces may cause problems such as deterioration of a medical device due to friction, inflammation of a living body, and the like.

In view of this, for improvement of the surface lubricity of a device, there have been proposed methods in which a functional group is generated on the surface of a device by performing an ozone treatment or a plasma treatment and a hydrophilic polymer is subsequently graft-polymerized on the device (Patent Documents 1 and 2). Further, a method of coating the surface of a medical equipment with a urethane resin having a hydrophilic moiety has been proposed (Patent Document 3).

(II) Adherent cells such as macrophages and fibroblasts are called "anchorage-dependent cells" since they are activated and proliferate only when they adhere to an adherend. Adhesion of these cells is induced via protein families (adherent molecules and proteins) found in the extracellular matrix, such as vitronectin and fibronectin. Such cell adhesion presents problems in various fields, including the medical field.

For example, fibroblasts added to a culture medium adhere to a tissue culture plate via extracellular matrix proteins. Similarly, in urinary catheters, bacterial cells adhere to the catheter wall and, for example, platelets adhere to the tip of an arterial catheter and, on contact lenses, such adhesion creates a state where cells cover the lens surface via proteins. The occurrence of such cell adhesion in a medical equipment, an apparatus or the like in this manner creates major problems since it not only simply causes contamination but also results in, for example, clogging and reduction in analysis accuracy and sensitivity.

In view of this, as a technology for inhibiting non-specific adhesion of a biological substance to a container, a copolymer of 2-methacryloyloxyethyl phosphorylcholine and a methacrylic acid ester has been described to make adhesion and aggregation of platelets as well as adhesion of plasma proteins unlikely to occur (Patent Document 4).

Further, as a protein adsorption inhibitor, for example, a copolymer of 2-methacryloyloxyethyl phosphorylcholine with n-butyl (meth)acrylate, methyl (meth)acrylate or styrene has been described (Patent Document 5).

For anchorage-dependent cells, basically, a monolayer culture method is mainly employed; however, the resulting cultured cells often have properties different from their in vivo properties. For example, in the industrial application of a protein or the like produced by such cells, it is known that, by three-dimensionally culturing the cells and thereby forming cell clusters, functions closer to those of the cells existing in a biological tissue can be exerted (Non-patent Document 1). Conventionally, as methods forming a cell cluster, for example, hanging-drop method, gyratory culture method, methyl cellulose method, and three-dimensional sphere method have been known.

(III) Microchannel devices have many advantages in that, for example, they are available in small quantities and many types and have high efficiency and low environmental load; therefore, in recent years, such microchannel devices have been utilized for the synthesis, analysis, extraction, separation and the like of substances. As the substrate materials of these devices, glasses and resins are known. Thereamong, silicone rubber substrates are useful since they can be easily micro-processed and have excellent optical transparency and chemical resistance.

The above-described devices usually have a 0.1 µm to 1 mm microchannel, and transfer, reaction or measurement of a liquid, microparticles, gel substance or the like is performed inside of this channel. Such devices enable to perform, for example, the measurement and detection of a biological sample, such as a blood sample, in a short period of time.

However, since the channels of such microchannel devices are narrow, there is a problem that adhesion of a biological sample or the like to the channel surface is likely to cause a reduction in flow rate. In addition, adhesion of a sample component to the channel surface makes the channel even narrower, and the effects of the loss of a reagent or the like on measured values are not negligible. Furthermore, since silicone rubber substrates have a low affinity for water, when a liquid including water is allowed to flow in the channel, poor fluidity potentially makes it impossible to accurately perform a desired operation. Therefore, it is necessary to hydrophilize the channel surface so as to inhibit the adhesion of a sample component thereto.

In view of this, for the purposes of improving the wettability of a microchannel with water, preventing a chemical liquid from remaining in a micropump and stabilizing the quantitative accuracy or detection accuracy, it has been proposed to form a layer of a sulfur compound having a hydrophilic group as a terminal group on a metal layer surface of a microchannel (Patent Document 6). Further, it has been also proposed to modify the inner wall surface of a microchannel with a fluororesin or the like (Patent Document 7), and to coat the surface with polyethylene glycol, Eval, Poval, or a polymer having a phosphorylcholine group (Patent Document 8).

RELATED ART DOCUMENTS

Patent Documents

[Patent Document 1] Japanese Patent No. 3131950
[Patent Document 2] JP H5-168695 A

[Patent Document 3] Japanese Translated PCT Patent Application Laid-open No. H11-506375
[Patent Document 4] Japanese Patent No. 2890316
[Patent Document 5] Japanese Patent No. 3443891
[Patent Document 6] JP 2001-252896 A
[Patent Document 7] JP 2005-125280 A
[Patent Document 8] JP 2008-82961 A Non-Patent Document

[Non-patent Document 1] Roberts R. A. and Soames A. R., Fundam Appl Toxicol. 1993 21(2): 149-158

SUMMARY OF THE INVENTION

Problems to be Solved by the Invention

However, the methods described in Patent Documents 1 and 2 are not preferred because of the side effects, such as a reduction in durability and deterioration of the mechanical properties of the resulting substrate. Moreover, the method described in Patent Document 3 has a problem in that the resulting surface is not sufficient in terms of the peeling resistance and the lubricity in a wet state.

Therefore, an object of the present invention (I) is to provide: a composition with which a medical device whose surface has sufficient lubricity and excellent durability can be produced; a medical device having a modified surface; and a method of producing the medical device having a modified surface.

The methods described in Patent Documents 4 and 5 do not necessarily provide a sufficient cell adhesion-inhibiting effect.

Moreover, with regard to Non-patent Document 1, such studies on various anchorage-dependent cells have not been done enough, and an equipment on which cell clusters of a wide range of anchorage-dependent cells can be formed in a substantially universal manner is yet to be discovered.

Therefore, an object of the present invention (II) is to provide: a cell adhesion inhibitor which has low cytotoxicity and excellent cell adhesion-inhibiting effect; and an equipment which has these effects, and another object of the present invention (II) is to provide: a culture equipment on which a cell cluster can be easily produced; and a method by which a cell cluster can be easily produced.

Furthermore, the coatings described in Patent Documents 6 to 8 do not necessarily provide a sufficient effect of inhibiting adhesion of a sample component such as a biological sample.

The present invention (III) was made in view of this problems, and an object of the present invention (III) is to provide: a silicone substrate which has a hydrophilic surface to which a sample component is unlikely to adhere; a composition which can easily form a silicone substrate having a microchannel; and a method of producing the substrate.

Technical Solution

The present inventors intensively studied to discover that the above-described problems can be solved by a composition which comprises a polymer containing a hydrophilic repeating unit and a repeating unit that has a polyoxyalkylene group in a side chain and a specific group at the terminal of the side chain, thereby completing the present invention.

Examples of the constitution of the present invention (I) include the following [1] to [10].

[1] A medical device composition, comprising a polymer having the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[2] The medical device composition according to [1], wherein the repeating unit (A) is at least one selected from a repeating unit (A-1) which has a polyoxyalkylene group in a side chain whose terminal is constituted by a hydrogen atom or an alkyl group having 1 to 4 carbon atoms, a repeating unit (A-2) which has an ammonioalkyl phosphate group at a side chain terminal, a repeating unit (A-3) which has an amide group in a side chain, a repeating unit (A-4) which has a heterocycle containing nitrogen and oxygen at a side chain terminal, a repeating unit (A-5) which has a lactam in a side chain, a repeating unit (A-6) which has a betaine group at a side chain terminal, an anionic repeating unit (A-7), and a cationic repeating unit (A-8).

[3] The medical device composition according to [1] or [2], wherein the repeating unit (A) is at least one selected from the repeating unit (A-1) represented by the below-described Formula (1), the repeating unit (A-2) represented by the below-described Formula (2), the repeating unit (A-3) represented by the below-described Formula (3), the repeating unit (A-4) represented by the below-described Formula (4), the repeating unit (A-5) represented by the below-described Formula (5), the repeating unit (A-6) represented by the below-described Formula (6), the anionic repeating unit (A-7), and the repeating unit (A-8) represented by the below-described Formula (8):

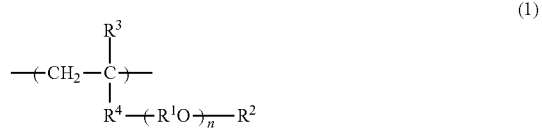

[wherein, $R^1$ represents an alkylene group having 2 to 4 carbon atoms; $R^2$ represents a hydrogen atom or an alkyl group having 1 to 4 carbon atoms; $R^3$ represents a hydrogen atom or a methyl group; $R^4$ represents —O—, *—(C=O)—O—, *—(C=O)—NR$^5$—, *—NR$^5$—(C=O)—($R^5$ represents a hydrogen atom or an organic group having 1 to 10 carbon atoms, and * represents a position at which the group is bound to a carbon atom bound with $R^3$ in Formula (1)), or a phenylene group; and n represents 2 to 100 as an average value];

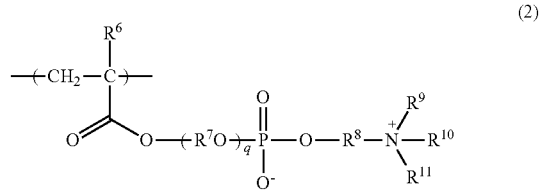

[wherein, $R^6$ represents a hydrogen atom or a methyl group; $R^7$ represents an alkylene group having 2 to 4 carbon atoms; $R^8$ represents an alkylene group having 1 to 10 carbon atoms; $R^9$, $R^{10}$ and $R^{11}$ each independently represent a hydrogen atom or a hydrocarbon group having 1 to 8 carbon atoms; and q represents 1 to 10 as an average value];

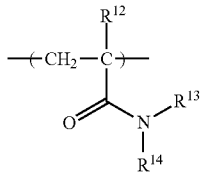
(3)

[wherein, $R^{12}$ represents a hydrogen atom or a methyl group; and $R^{13}$ and $R^{14}$ each independently represent a hydrogen atom, an alkyl group having 1 to 6 carbon atoms or hydroxyalkyl group];

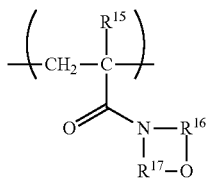
(4)

[wherein, $R^{15}$ represents a hydrogen atom or a methyl group; and $R^{16}$ and $R^{17}$ each independently represent an alkylene group having 1 to 3 carbon atoms];

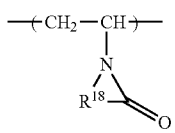
(5)

[wherein, $R^{18}$ represents an alkylene group having 1 to 5 carbon atoms];

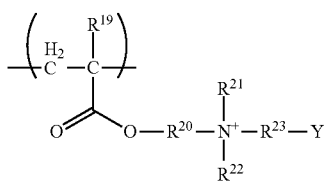
(6)

[wherein, Y represents —(C═O)O, —(O═S═O)O, —O(O═S═O)O, —(S═O)O, —O(S═O)O, —OP(═O)(OR$^{24}$)O, —OP(═O) (R$^{24}$) O, —P(═O) (OR$^{24}$)O, or —P(═O) (R$^{24}$)O—(R$^{24}$ represents an alkyl group having 1 to 3 carbon atoms); $R^{19}$ represents a hydrogen atom or a methyl group; $R^{20}$ represents a divalent organic group having 1 to 10 carbon atoms; $R^{21}$ and $R^{22}$ each independently represent a hydrocarbon group having 1 to 10 carbon atoms; and $R^{23}$ represents a divalent organic group having 1 to 10 carbon atoms]; and

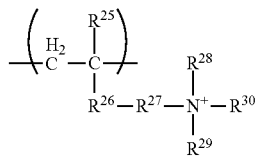
(8)

[wherein, $R^{25}$ represents a hydrogen atom or a methyl group; $R^{26}$ represents —O—, *—(C═O)—O—, *—(C═O)—NR$^{31}$—, *—NR$^{31}$—(C═O)—(R$^{31}$ represents a hydrogen atom or an organic group having 1 to 10 carbon atoms, and * represents a position at which the group is bound to a carbon atom bound with $R^{25}$ in Formula (8)), or a phenylene group; $R^{27}$ represents a divalent organic group having 1 to 10 carbon atoms; and $R^{28}$, $R^{29}$ and $R^{30}$ each independently represent a hydrocarbon group having 1 to 10 carbon atoms].

[4] The medical device composition according to any one of [1] to [3], wherein the repeating unit (B) is a repeating unit derived from a monomer having an ethylenically unsaturated bond.

[5] The medical device composition according to any one of [1] to [4], wherein the repeating unit (B) is represented by the following Formula (b2):

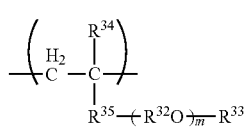
(b2)

[wherein, $R^{32}$ represents an alkylene group having 2 to 4 carbon atoms; $R^{33}$ represents an alkyl group having 5 to 30 carbon atoms, an alkanoyl group having 5 to 30 carbon atoms, or an aryl group having 6 to 30 carbon atoms; $R^{34}$ represents a hydrogen atom or amethyl group; $R^{35}$ represents —O—, —(C═O)—O—, —(C═O)—NR$^{36}$—, —NR$^{36}$—(C═O)—(R$^{36}$ represents a hydrogen atom or an organic group having 1 to 10 carbon atoms, and  represents a position at which the group is bound to a carbon atom bound with $R^{34}$ in Formula (b2)), or a phenylene group; and m represents 2 to 100 as an average value].

[6] The medical device composition according to any one of [1] to [5], the polymer further comprises at least one repeating unit (C) selected from a repeating unit (C-1) represented by the following Formula (c1) and a repeating unit (C-2) having a group represented by the following Formula (c2) at a side chain terminal:

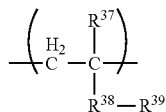
(c1)

[wherein, $R^{37}$ represents a hydrogen atom or a methyl group; $R^{38}$ represents —O—, *—(C═O)—O—, *—(C═O)—NR$^{40}$—, *—NR$^{40}$—(C═O)—(R$^{40}$ represents a hydrogen atom or an organic group having 1 to 10 carbon atoms, and * represents a position at which the group is bound to a carbon atom bound with $R^{37}$ in Formula (c1)), or a phenylene group; and $R^{39}$ represents a hydrocarbon group having 4 to 30 carbon atoms]; and

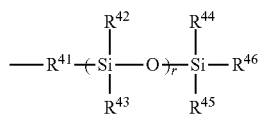
(c2)

[wherein, $R^{41}$ represents a divalent organic group having 1 to 10 carbon atoms; $R^{42}$ and $R^{43}$ each independently represent an organic group having 1 to 10 carbon atoms; $R^{44}$, $R^{45}$ and $R^{46}$ each independently represent —OSi($R^{49}$)$_3$ ($R^{49}$s each independently represent a hydrogen atom or an organic group having 1 to 8 carbon atoms), or an organic group having 1 to 10 carbon atoms; and r represents 0 to 200 as an average value].

[7] The medical device composition according to any one of [1] to [6], wherein the polymer is soluble in water.

[8] A medical device comprising, on at least a part of a surface thereof, a polymer having the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[9] A medical device comprising a cross-linked product of a polymer having the following repeating units (A) and (B) on at least a part of the surface of a substrate:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[10] A method of producing a medical device, the method comprising a step of arranging a polymer having the following repeating units (A) and (B) on at least a part of the surface of the medical device:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

Examples of the constitution of the present invention (II) include the following [11] to [20].

[11] A cell adhesion inhibitor comprising a polymer having the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[12] The cell adhesion inhibitor according to [11], wherein the repeating unit (A) is at least one selected from a repeating unit (A-1) which has a polyoxyalkylene group in a side chain whose terminal is constituted by a hydrogen atom or an alkyl group having 1 to 4 carbon atoms, a repeating unit (A-2) which has an ammonioalkyl phosphate group at a side chain terminal, a repeating unit (A-3) which has an amide group in a side chain, a repeating unit (A-4) which has a heterocycle containing nitrogen and oxygen at a side chain terminal, a repeating unit (A-5) which has a lactam in a side chain, a repeating unit (A-6) which has a betaine group at a side chain terminal, an anionic repeating unit (A-7), and a cationic repeating unit (A-8).

[13] The cell adhesion inhibitor according to [11] or [12], wherein the repeating unit (A) is at least one selected from the repeating unit (A-1) represented by Formula (1), the repeating unit (A-2) represented by Formula (2), the repeating unit (A-3) represented by Formula (3), the repeating unit (A-4) represented by Formula (4), the repeating unit (A-5) represented by Formula (5), the repeating unit (A-6) represented by Formula (6), the anionic repeating unit (A-7), and the repeating unit (A-8) represented by Formula (8).

[14] The cell adhesion inhibitor according to any one of [11] to [13], wherein the repeating unit (B) is a repeating unit derived from a monomer having an ethylenically unsaturated bond.

[15] The cell adhesion inhibitor according to any one of [11] to [14], wherein the repeating unit (B) is represented by the above-described Formula (b2).

[16] The cell adhesion inhibitor according to any one of [11] to [15], wherein the polymer further comprises at least one repeating unit (C) selected from the above-described repeating unit (C-1) represented by Formula (c1) and the above-described repeating unit (C-2) having a group represented by Formula (c2) at a side chain terminal.

[17] The cell adhesion inhibitor according to any one of [11] to [16], wherein the polymer is soluble in water.

[18] A cell culture equipment comprising, on at least a part of a surface thereof, a polymer having the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[19] A method of producing a cell culture equipment, the method comprising a step of arranging a polymer having the following repeating units (A) and (B) on at least a part of a surface of the cell culture equipment:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[20] A method of producing a cell cluster, the method comprising culturing cells using the cell culture equipment according to [18] and thereby forming a cell cluster.

Examples of the constitution of the present invention (III) include the following [21] to [31].

[21] A silicone substrate treatment composition comprising a polymer having the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[22] The silicone substrate treatment composition according to [21], wherein the repeating unit (A) is at least one selected from a repeating unit (A-1) which has a polyoxyalkylene group in a side chain whose terminal is constituted by a hydrogen atom or an alkyl group having 1 to 4 carbon atoms, a repeating unit (A-2) which has an ammonioalkyl phosphate group at a side chain terminal, a repeating unit (A-3) which has an amide group in a side chain, a repeating unit (A-4) which has a heterocycle containing nitrogen and oxygen at a side chain terminal, a repeating unit (A-5) which has a lactam in a side chain, a repeating unit (A-6) which has a betaine group at a side chain terminal, an anionic repeating unit (A-7), and a cationic repeating unit (A-8).

[23] The silicone substrate treatment composition according to [21] or [22], wherein the repeating unit (A) is at least one selected from the repeating unit (A-1) represented by Formula (1), the repeating unit (A-2) represented by Formula (2), the repeating unit (A-3) represented by Formula (3), the repeating unit (A-4) represented by Formula (4), the repeating unit (A-5) represented by Formula (5), the repeating unit (A-6) represented by Formula (6), the anionic repeating unit (A-7), and the repeating unit (A-8) represented by Formula (8).

[24] The silicone substrate treatment composition according to any one of [21] to [23], wherein the repeating unit (B) is a repeating unit derived from a monomer having an ethylenically unsaturated bond.

[25] The silicone substrate treatment composition according to any one of [21] to [24], wherein the repeating unit (B) is represented by the above-described Formula (b2).

[26] The silicone substrate treatment composition according to any one of [21] to [25], wherein the polymer further comprises at least one repeating unit (C) selected from the above-described repeating unit (C-1) represented by Formula (c1) and the above-described repeating unit (C-2) having a group represented by Formula (c2) at a side chain terminal.

[27] The silicone substrate treatment composition according to any one of [21] to [26], wherein the polymer is soluble in water.

[28] A silicone substrate comprising a polymer having the following repeating units (A) and (B) on at least a part of a surface of the substrate:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[29] A silicone substrate having a microchannel, the silicone substrate comprising a polymer having the following repeating units (A) and (B) on at least a part of a surface of the substrate:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[30] A method of producing a silicone substrate, the method comprising a step of arranging a polymer having the following repeating units (A) and (B) on at least a part of the silicone substrate:
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[31] The method according to [30], wherein the silicone substrate is a silicone substrate having a microchannel.

Advantageous Effects of the Invention

According to the present invention (I), a medical device having excellent lubricity and excellent durability can be easily provided.

The cell adhesion inhibitor of the present invention (II) has low cytotoxicity and exhibits excellent cell adhesion-inhibiting effect. Therefore, according to the present invention (II), an equipment and an apparatus that have a modified surface on which cells are unlikely to be killed and to which cells are unlikely to adhere can be provided, and a cell culture equipment which maintains these effects over a long period can be provided.

In addition, according to the present invention (II), a cell cluster can be easily produced.

According to the silicone substrate treatment composition of the present invention (III), excellent hydrophilicity and sample component adhesion-inhibiting effect, particularly a biological sample adhesion-inhibiting effect, can be imparted to a silicone substrate. In addition, since a polymer contained in this composition exhibits high adsorption to a silicone substrate and is thus unlikely to be peeled off therefrom, the above-described effects can be maintained for a long time.

Therefore, the silicone substrate treatment composition of the present invention (III) is useful as a composition for coating a silicone substrate.

Moreover, according to the silicone substrate production method of the present invention (III), a silicone substrate to which a sample component, particularly a biological sample, is unlikely to adsorb and which has excellent sustainability of this effect can be produced in a simple manner.

MODE FOR CARRYING OUT THE INVENTION

<<Polymer Composition>>

The polymer composition according to the present invention (hereinafter, also referred to as "the present composition") is a composition which comprises a polymer having the below-described repeating units (A) and (B) and is one selected from the group consisting of a medical device composition, a cell adhesion inhibitor, and a silicone substrate treatment composition.

In the present invention, a polymer composition consisting of only the above-described polymer is also referred to as "composition".

The present invention (I) relates to a medical device composition which imparts a medical device with lubricity and excellent durability.

The reason why such an effect is exerted is not necessarily clear; however, it is speculated that the polymer adsorbs to the wall surface of the medical device via the repeating unit (B) or the repeating units (B) and (C) while the wall surface is hydrophilized by the repeating units (A) and (B) to form a thick hydrophilic layer, whereby lubricity is expressed.

Further, according to the present invention (I), not only lubricity is imparted but also adsorption of biological substances, such as proteins, lipids and nucleic acids, can be inhibited.

The medical device composition is believed to exert the above-described effects because of the specific polymer. Therefore, the polymer can be directly used as a medical device composition, or can be used as a material for producing a medical device composition.

The present invention (II) relates to a cell adhesion inhibitor which has low cytotoxicity and exhibits excellent cell adhesion-inhibiting effect.

The polymer has low cytotoxicity even when it exists on a surface of a cell culture equipment, and the polymer arranged on the equipment surface is not easily peeled off from the equipment; however, even if the polymer is peeled off, it maintains low cytotoxicity. Therefore, the cell adhesion inhibitor can be suitably used on an equipment for cell culture.

The reason why such an effect can be exerted is not necessarily clear; however, it is speculated that the polymer adsorbs to the wall surface of an equipment, an apparatus or the like via the repeating unit (B) or the repeating units (B) and (C) while the wall surface is hydrophilized by the repeating units (A) and (B) and adsorption of proteins, lipids and the like is thus further inhibited, whereby adhesion of cells can be suppressed.

Therefore, the polymer can be directly used as a cell adhesion inhibitor, or can be used as a material for producing a cell adhesion inhibitor. Further, such a cell adhesion inhibitor is also capable of inhibiting adhesion of not only cells but also biological substances, such as proteins, lipids and nucleic acids.

It is noted here that, in the present invention (II), inhibition of cell adhesion refers to inhibition of adhesion between adherent cells, such as anchorage-dependent cells, and various (equipment) surfaces and the like with which the cells come into contact.

Examples of the cells include anchorage-dependent cells and suspended cells (e.g., blood cells, such as leukocytes, erythrocytes, and platelets). Examples of the anchorage-dependent cells include cancer cells, such as HeLa cells and F9 cells; fibroblasts, such as 3T3 cells; stem cells, such as ES cells, iPS cells, and mesenchymal stem cells; renal cells, such as HEK293 cells; nerve cells, such as NT2 cells; endothelial cells, such as UW cells and HMEC-1 cells; myocardial cells, such as H9c2 cells; and epithelial cells, such as Caco-2 cells.

The present invention (III) relates to a silicone substrate treatment composition.

<Polymer>

The above-described polymer comprises the following repeating units (A) and (B):
(A) a hydrophilic repeating unit; and
(B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

[Repeating Unit (A)]

The repeating unit (A) is not particularly restricted as long as it is a hydrophilic repeating unit and different from the repeating unit (B); however, the repeating unit (A) is preferably at least one selected from a repeating unit (A-1) which has a polyoxyalkylene group in a side chain whose terminal is constituted by a hydrogen atom or an alkyl group having 1 to 4 carbon atoms, a repeating unit (A-2) which has an ammonioalkyl phosphate group at a side chain terminal, a repeating unit (A-3) which has an amide group in a side chain, a repeating unit (A-4) which has a heterocycle containing nitrogen and oxygen at a side chain terminal, a repeating unit (A-5) which has a lactam in a side chain, a repeating unit (A-6) which has a betaine group at a side chain terminal, an anionic repeating unit (A-7), and a cationic repeating unit (A-8).

By incorporating such a repeating unit (A) into the polymer:
a medical device having excellent lubricity can be easily obtained;
an equipment and an apparatus that have a hydrophilic surface can be easily obtained and, therefore, an equipment and an apparatus that exhibit excellent cell adhesion-inhibiting properties can be easily obtained; and
a silicone substrate that has excellent surface hydrophilicity and exhibits excellent properties of inhibiting adhesion of a sample component, particularly a biological sample, can be easily obtained.

It is noted here that the term "hydrophilic repeating unit" used herein means a repeating unit which has a strong affinity for water. Specifically, when a homopolymer consisting of only one type of repeating unit that is the same as a repeating unit constituting a polymer (which homopolymer has a number-average molecular weight of about 10,000 as determined by the measurement method described in the section of Examples) has a solubility of 1 g or greater in 100 g of pure water at normal temperature (25° C.) the repeating unit is regarded as hydrophilic.

(Repeating Unit (A-1))

The repeating unit (A-1) has a polyoxyalkylene group in a side chain, and the terminal of the side chain is constituted by a hydrogen atom or an alkyl group having 1 to 4 carbon atoms.

The repeating unit (A-1) is preferably a repeating unit having a structure represented by the following Formula (1') at a side chain terminal. Examples of the repeating unit having a structure represented by Formula (1') at a side chain terminal include known repeating units, among which (meth)acrylate repeating units, (meth)acrylamide repeating units, and styrene repeating units are preferred. Particularly, a repeating unit represented by the below-described Formula (1) is preferred.

[wherein, $R^1$ represents an alkylene group having 2 to 4 carbon atoms; $R^2$ represents a hydrogen atom or an alkyl group having 1 to 4 carbon atoms; and n represents 2 to 100 as an average value]

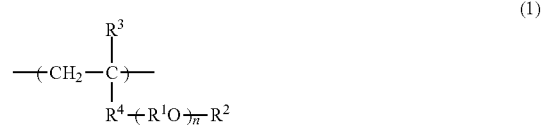

[wherein, $R^1$, $R^2$ and n have the same meanings as in Formula (1'); $R^3$ represents a hydrogen atom or a methyl group; and $R^4$ represents —O—, *—(C=O)—O—, *—(C=O)—NR$^5$—, *—NR$^5$—(C=O)— ($R^5$ represents a hydrogen atom or an organic group having 1 to 10 carbon atoms, and * represents a position at which the group is bound to the carbon atom bound with $R^3$ in Formula (1)), or a phenylene group]

The n $R^1$s may be the same or different, and the plural $R^1$s contained in the repeating unit may be the same or different. Hereinafter, for other symbols used in each structural unit as well, plural groups represented by the same symbol contained in a repeating unit may be the same or different. That is, for example, plural $R^e$s contained in the repeating unit may the same as or different from each other.

The number of carbon atoms of the alkylene group represented by $R^1$ is preferably 2 or 3, more preferably 2.

The alkylene group represented by $R^1$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Thereamong, from the standpoints of, for example, availability and attaining excellent lubricity-imparting performance and hydrophilization performance, an ethane-1,2-diyl group is preferred.

From the standpoints of, for example, availability and attaining excellent lubricity-imparting performance and hydrophilization performance, the number of carbon atoms of the alkyl group represented by $R^2$ is preferably 1 to 3, more preferably 1 or 2, still more preferably 1. The alkyl group represented by $R^2$ may be linear or branched, and specific examples thereof include a methyl group, an ethyl group, an n-propyl group, an isopropyl group, an n-butyl group, an isobutyl group, a sec-butyl group, and a tert-butyl group.

Among these groups of $R^2$, from the standpoints of, for example, availability and attaining excellent lubricity-imparting performance and hydrophilization performance, $R^2$ is preferably a hydrogen atom or an alkyl group having 1 to 3 carbon atoms, more preferably a hydrogen atom or an alkyl group having 1 or 2 carbon atoms, still more preferably a hydrogen atom or a methyl group, particularly preferably a methyl group.

Examples of the phenylene group represented by $R^4$ include a 1,2-phenylene group, a 1,3-phenylene group, and a 1,4-phenylene group.

The number of carbon atoms of the organic group represented by $R^5$ is preferably 1 to 6. The organic group is, for example, a hydrocarbon group. The term "hydrocarbon group" is a concept that encompasses aliphatic hydrocarbon groups, alicyclic hydrocarbon groups, and aromatic hydrocarbon groups.

An aliphatic hydrocarbon group represented by $R^5$ may be linear or branched, and specific examples thereof include alkyl groups, such as a methyl group, an ethyl group, an n-propyl group, an isopropyl group, an n-butyl group, an isobutyl group, a sec-butyl group, a Cert-butyl group, a pentyl group, a hexyl group, a heptyl group, an octyl group, a nonyl group, and a decyl group.

The alicyclic hydrocarbon groups are generally classified into monocyclic alicyclic hydrocarbon groups and bridged cyclic hydrocarbon groups. Examples of the monocyclic alicyclic hydrocarbon groups include cycloalkyl groups, such as a cyclopropyl group and a cyclohexyl group. Examples of the bridged cyclic hydrocarbon groups include an isobornyl group.

Examples of the aromatic hydrocarbon groups include aryl groups, such as a phenyl group.

Among of $R^4$, from the standpoint of, for example, attaining excellent lubricity-imparting performance and hydrophilization performance, $R^4$ is preferably *—(C=O)—O— or a phenylene group, particularly preferably *—(C=O)—O—.

The n is preferably 4 to 90, more preferably 8 to 90, still more preferably 8 to 60, yet still more preferably 8 to 40, particularly preferably 9 to 25, as an average value.

It is noted here that each "average value" used herein can be measured by NMR. For example, with regard to the structure of the above-described Formula (1), the average value of n can be determined by measuring $^1$H-NMR and comparing the integral values of the proton peaks obtained for the alkylene group having 2 to 4 carbon atoms of $R^1$ and the terminal methyl group of the alkyl group having 1 to 4 carbon atoms of $R^2$.

Examples of a monomer from which the repeating unit (A-1) is derived include polyethylene glycol (meth)acrylate, polypropylene glycol (meth)acrylate, polyethylene glycol polytetramethylene glycol (meth)acrylate, polypropylene glycol polytetramethylene glycol (meth)acrylate, methoxypolyethylene glycol (meth)acrylate, and ethoxypolyethylene glycol (meth)acrylate, among which polyethylene glycol (meth)acrylate and methoxypolyethylene glycol (meth)acrylate are preferred.

The repeating unit (A-1) is, for example, a repeating unit obtained by using any one of these monomers individually, or two or more of the monomers in combination.

(Repeating Unit (A-2))

The repeating unit (A-2) is a repeating unit having an ammonioalkyl phosphate group at a side chain terminal. The repeating unit (A-2) is preferably a repeating unit represented by the following Formula (2):

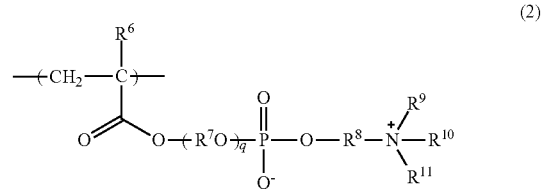

[wherein, $R^6$ represents a hydrogen atom or a methyl group; $R^7$ represents an alkylene group having 2 to 4 carbon atoms; $R^8$ represents an alkylene group having 1 to 10 carbon atoms; $R^9$, $R^{10}$ and $R^{11}$ each independently represent a hydrogen atom or a hydrocarbon group having 1 to 8 carbon atoms; and q represents 1 to 10 as an average value].

The number of carbon atoms of the alkylene group represented by $R^7$ is preferably 2 or 3, more preferably 2.

The alkylene group represented by $R^7$ may be linear or branched, and examples thereof include the same groups as those exemplified above for $R^1$. Thereamong, from the standpoints of, for example, availability and attaining excellent lubricity-imparting performance and hydrophilization performance, an ethane-1,2-diyl group is preferred.

When there are plural $R^7$s, the plural $R^7$s may be the same or different.

The number of carbon atoms of the alkylene group represented by $R^8$ is preferably 1 to 6, more preferably 1 to 4, still more preferably 2 or 3, particularly preferably 2.

The alkylene group represented by $R^8$ may be linear or branched, and preferred specific examples thereof include the same groups as those exemplified above for the alkylene group represented by $R^7$.

It is preferred that $R^9$, $R^{10}$ and $R^{11}$ be each independently a hydrocarbon group having 1 to 8 carbon atoms. The number of carbon atoms of this hydrocarbon group is preferably 1 to 4, more preferably 1 or 2, particularly preferably 1.

Examples of the hydrocarbon group include alkyl groups; aryl groups such as a phenyl group; and aralkyl groups such as a benzyl group, and the hydrocarbon group is preferably an alkyl group.

This alkyl group may be linear or branched, and preferred specific examples thereof include a methyl group, an ethyl group, an n-propyl group, an isopropyl group, an n-butyl group, an isobutyl group, a sec-butyl group, and a Cert-butyl group.

The q is preferably 1 to 7, more preferably 1 to 4, particularly preferably 1, as an average value.

The repeating unit (A-2) may also have an alkali metal ion, such as a sodium ion or a potassium ion; an alkaline earth metal ion, such as a calcium ion or a magnesium ion; or a counter ion, such as an ammonium ion, a hydrogen ion or a hydroxide ion.

Examples of a monomer from which the repeating unit (A-2) is derived include
2-(meth)acryloyloxyethyl-2'-(trimethylammonio)ethyl phosphate (2-(meth)acryloyloxyethyl phosphorylcholine),
3-(meth)acryloyloxypropyl-2'-(trimethylammonio)ethyl phosphate,
4-(meth)acryloyloxybutyl-2'-(trimethylammonio)ethyl phosphate,
2-(meth)acryloyloxyethoxyethyl-2'-(trimethylammonio) ethyl phosphate,
2-(meth)acryloyloxydiethoxyethyl-2'-(trimethylammonio) ethyl phosphate, 2-(meth)acryloyloxyethyl-2'-(triethylammonio)ethyl phosphate, and
2-(meth)acryloyloxyethyl-2'-(tributylammonio)ethyl phosphate.

The repeating unit (A-2) is, for example, a repeating unit obtained by using any one of these monomers individually, or two or more of the monomers.

(Repeating Unit (A-3))

The repeating unit (A-3) is a repeating unit having an amide group in a side chain. The repeating unit (A-3) is preferably a repeating unit represented by the following Formula (3):

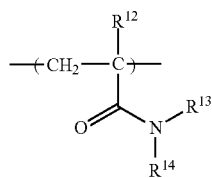

(3)

[wherein, $R^{12}$ represents a hydrogen atom or a methyl group; and $R^{13}$ and $R^{14}$ each independently represent a hydrogen atom, or an alkyl group having 1 to 6 carbon atoms or hydroxyalkyl group].

The number of carbon atoms of the alkyl groups represented by $R^{13}$ and $R^{14}$ is preferably 1 to 3.

The alkyl groups may be linear or branched, and preferred specific examples thereof include a methyl group, an ethyl group, an n-propyl group, and an isopropyl group.

The number of carbon atoms of the hydroxyalkyl groups represented by $R^{13}$ and $R^{14}$ is preferably 1 to 6, more preferably 1 to 3. The alkyl groups contained in the hydroxyalkyl groups may be linear or branched, and preferred specific examples of the hydroxyalkyl groups include a hydroxymethyl group, a hydroxyethyl group, a hydroxypropyl group, and a hydroxyisopropyl group. It is noted here that, in the hydroxyalkyl groups, the hydroxyl group may be at any substitution position.

Examples of a monomer from which the repeating unit (A-3) is derived include dimethyl (meth)acrylamide, diethyl (meth)acrylamide, N-isopropyl (meth)acrylamide, N-(hydroxymethyl) (meth)acrylamide, and N-(2-hydroxyethyl) (meth)acrylamide.

The repeating unit (A-3) is, for example, a repeating unit obtained by using any one of these monomers individually, or two or more of the monomers.

(Repeating Unit (A-4))

The repeating unit (A-4) is a repeating unit which has a heterocycle containing nitrogen and oxygen at a side chain terminal. The repeating unit (A-4) is preferably a repeating unit represented by the following Formula (4):

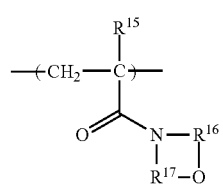

(4)

[wherein, $R^5$ represents a hydrogen atom or a methyl group; and $R^{16}$ and $R^{17}$ each independently represent an alkylene group having 1 to 3 carbon atoms].

The number of carbon atoms of the alkylene groups represented by $R^{16}$ and $R^{17}$ is preferably 1 or 2.

The alkylene groups may be linear or branched; however, they are preferably linear. Preferred specific examples thereof include a methane-1,1-diyl group and an ethane-1,2-diyl group.

Examples of a monomer from which the repeating unit (A-4) is derived include 4-(meth)acryloyl morpholine.

The repeating unit (A-4) is, for example, a repeating unit obtained by using this monomer individually, or two or more of thereof.

(Repeating Unit (A-5))

The repeating unit (A-5) is a repeating unit having a lactam in a side chain. The repeating unit (A-5) is preferably a repeating unit represented by the following Formula (5):

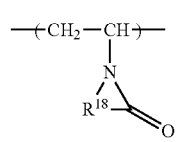

(5)

[wherein, $R^{18}$ represents an alkylene group having 1 to 5 carbon atoms].

The number of carbon atoms of the alkylene group represented by $R^{18}$ is preferably 3 to 5.

The alkylene group may be linear or branched; however, it is preferably linear. Preferred specific examples thereof include a propane-1,3-diyl group, a butane-1,4-diyl group, and a pentane-1,5-diyl group.

Examples of a monomer from which the repeating unit (A-5) is derived include 1-vinyl-2-pyrrolidone and N-vinyl-ε-caprolactam.

The repeating unit (A-5) is, for example, a repeating unit obtained by using one of these monomers individually, or two or more of the monomers.

(Repeating Unit (A-6))

The repeating unit (A-6) is a repeating unit having a betaine group at a side chain terminal. The repeating unit (A-6) is preferably a repeating unit represented by the following Formula (6):

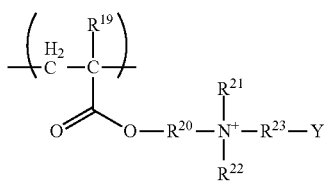

(6)

[wherein, Y represents —(C=O)O, —(O=S=O)O, —O(O=S=O)O, —(S=O)O, —O(S=O)O, —OP(=O) (OR$^{24}$)O, —OP(=O) (R$^{24}$)O, —P(=O) (OR$^{24}$)O, or —P(=O) (R$^{24}$)O— (R$^{24}$ represents an alkyl group having 1 to 3 carbon atoms); R$^{19}$ represents a hydrogen atom or a methyl group; R$^{20}$ represents a divalent organic group having 1 to 10 carbon atoms; R$^{21}$ and R$^{22}$ each independently represent a hydrocarbon group having 1 to 10 carbon atoms; and R$^{23}$ represents a divalent organic group having 1 to 10 carbon atoms]. [0116]

Y is preferably —(C=O)O. Examples of the alkyl group represented by R$^{24}$ include a methyl group, an ethyl group, an n-propyl group, and an isopropyl group.

The number of carbon atoms of the divalent organic groups represented by R$^{20}$ and R$^{23}$ is preferably 1 to 8, more preferably 1 to 6.

The divalent organic groups are preferably divalent hydrocarbon groups, more preferably divalent aliphatic hydrocarbon groups. The divalent aliphatic hydrocarbon groups may be linear or branched. As the divalent aliphatic hydrocarbon groups, alkanediyl groups are preferred. Examples thereof include a methane-1,1-diyl group, an ethane-1,2-diyl group, a propane-1,1-diyl group, a propane-1,2-diyl group, a propane-1,3-diyl group, a propane-2,2-diyl group, a butane-1,4-diyl group, a pentane-1,5-diyl group, and a hexane-1,6-diyl group.

The number of carbon atoms of the hydrocarbon groups represented by R$^{21}$ and R$^{22}$ is preferably 1 to 6, more preferably 1 to 4.

Examples of the hydrocarbon groups represented by R$^{21}$ and R$^{22}$ include alkyl groups; aryl groups such as a phenyl group; and aralkyl groups such as a benzyl group, and the hydrocarbon groups are preferably alkyl groups. The alkyl groups may be linear or branched, and examples thereof include a methyl group, an ethyl group, an n-propyl group, an isopropyl group, an n-butyl group, an isobutyl group, a sec-butyl group, and a Cert-butyl group.

The repeating unit (A-6) may also have an alkali metal ion, such as a sodium ion or a potassium ion; an alkaline earth metal ion, such as a calcium ion or a magnesium ion; or a counter ion, such as an ammonium ion, a hydrogen ion or a hydroxide ion.

Examples of a monomer from which the repeating unit (A-6) is derived include (meth)acrylate monomers, such as N-(meth)acryloyloxyethyl-N,N-dimethylammonium-α-N-methylcarbo xybetaine and N-(meth)acryloyloxyethyl-N,N-dimethylammonium-α-N-propylsulfo betaine.

The repeating unit (A-6) is, for example, a repeating unit obtained by using one of these monomers individually, or two or more of the monomers.

(Repeating Unit (A-7))

The repeating unit (A-7) is an anionic repeating unit.

Examples of the repeating unit (A-7) include acidic group-containing repeating units.

From the standpoints of, for example, ease of introduction and attaining excellent safety, the repeating unit (A-7) is preferably a unit derived from an ethylenically unsaturated bond-containing monomer.

Examples of the acidic group include a carboxyl group, a sulfo group, a phosphate group, and salts thereof, and the repeating unit (A-7) may have one, or two or more of these acidic groups. Examples of the salts include alkali metal salts, such as sodium salts and potassium salts; alkaline earth metal salts, such as magnesium salts and calcium salts; ammonium salts; and organic ammonium salts.

Examples of a monomer from which the repeating unit (A-7) is derived include unsaturated dicarboxylic acids, such as fumaric acid, maleic acid and itaconic acid, and salts thereof; unsaturated carboxylic acids such as (meth)acrylic acid, and salts thereof; sulfo group-containing polymerizable unsaturated monomers, such as ethylene sulfonic acid, allyl sulfonic acid, methallyl sulfonic acid, 2-sulfoethyl (meth)acrylate and 2-acrylamido-2-methylpropane sulfonic acid, and salts thereof; and phosphate group-containing polymerizable unsaturated monomers, such as 2-(meth) acryloyloxyethyl acid phosphate and 2-(meth)acryloyloxypropyl acid phosphate, and salts thereof. The repeating unit (A-7) can also be obtained using, for example, a hydrolysate of an acrylic acid ester; a hydrolysate of an unsaturated dicarboxylic acid anhydride, such as maleic anhydride or itaconic anhydride; or an adduct of an acidic group-containing thiol to an epoxy group of glycidyl methacrylate, (4-vinylbenzyl)glycidyl ether or the like.

Thereamong, (meth)acrylic acid is preferred because of its excellent ease of introduction, reactivity and the like.

The repeating unit (A-7) is, for example, a repeating unit obtained by using one of these monomers individually, or two or more of the monomers.

(Repeating Unit (A-8))

The repeating unit (A-8) is a cationic repeating unit. The repeating unit (A-8) is preferably a repeating unit represented by the following Formula (8):

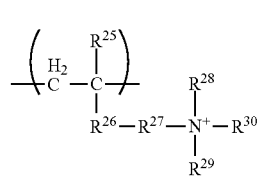

(8)

[wherein, R$^{25}$ represents a hydrogen atom or a methyl group; R$^{26}$ represents —O—, *—(C=O)—O—, *—(C=O)—NR$^{31}$—, *—NR$^{31}$—(C=O)—(R$^{31}$ represents a hydrogen atom or an organic group having 1 to 10 carbon atoms, and * represents a position at which the group is bound to the carbon atom bound with R$^{25}$ in Formula (8)), or a phenylene group; R$^{27}$ represents a divalent organic group having 1 to 10 carbon atoms; and R$^{28}$, R$^{29}$ and R$^{30}$ each independently represent a hydrocarbon group having 1 to 10 carbon atoms].

Examples of the phenylene group represented by R$^{26}$ include a 1,2-phenylene group, a 1,3-phenylene group, and a 1,4-phenylene group.

The number of carbon atoms of the organic group represented by R$^{31}$ is preferably 1 to 6. Examples of the organic group include hydrocarbon groups. Examples of the hydrocarbon groups include the same groups as those exemplified above for R$^{5}$.

The number of carbon atoms of the divalent organic group represented by R$^{27}$ is preferably 1 to 8, more preferably 1 to 6.

The divalent organic group is preferably a divalent hydrocarbon group, more preferably a divalent aliphatic hydrocarbon group. The divalent aliphatic hydrocarbon group may be linear or branched. Examples of the divalent aliphatic hydrocarbon group include the same groups as those exemplified above for $R^{20}$ and $R^{23}$.

The number of carbon atoms of the hydrocarbon groups represented by $R^{28}$, $R^{29}$ and $R^{30}$ is preferably 1 to 6, more preferably 1 to 4.

Examples of the hydrocarbon groups represented by $R^{28}$, $R^{29}$ and $R^{30}$ include the same groups as those exemplified above for $R^9$, $R^{10}$ and $R^{11}$.

The repeating unit (A-8) may also have a counter ion. Examples of the counter ion include halogen ions, such as a chlorine ion, a bromine ion, and an iodine ion; a hydrogen sulfide ion; alkyl sulfate ions, such as a methyl sulfate ion and an ethyl sulfate ion; alkyl sulfonate ions; aryl sulfonate ions, such as a dodecylbenzenesulfonate ion and a para-toluenesulfonate ion; alkenyl sulfonate ions, such as sodium 2-methyl-2-propene-1-sulfonate; and carboxylate ions, such as an acetate ion.

Preferred specific examples of a monomer from which the repeating unit (A-8) is derived include (meth)acrylates and (meth)acrylamides.

Examples of the monomer species of (meth)acrylates include ((meth)acryloyloxy-$C_{1-10}$ alkyl)-tri-$C_{1-10}$ alkyl ammonium chlorides such as ((meth) acryloyloxyethyl)trimethyl ammonium chloride; and ((meth)acryloyloxy-$C_{1-10}$ alkyl)-di-$C_{1-10}$ alkyl-$C_{6-10}$ aralkyl ammonium chlorides such as
((meth) acryloyloxyethyl)dimethylbenzyl ammonium chloride. Examples of the monomer species of (meth)acrylamides include (3-(meth)acrylamido-$C_{1-10}$ alkyl)-tri-$C_{1-10}$ alkyl ammonium chlorides such as (3-(meth) acrylamidopropyl)trimethyl ammonium chloride; and (3-(meth)acrylamido-$C_{1-10}$ alkyl)-di-$C_{1-10}$ alkyl-$C_{6-10}$ aralkyl ammonium chlorides such as
(3-(meth) acrylamidopropyl)dimethylbenzyl ammonium chloride. Thereamong, (3-(meth) acrylamidopropyl)trimethyl ammonium chloride is preferred because of its excellent ease of introduction and reactivity.

The repeating unit (A-8) is, for example, a repeating unit obtained by using any one of these monomers individually, or two or more of the monomers.

Among the above-described repeating units (A-1) to (A-8), from the standpoint of, for example, attaining excellent lubricity-imparting performance, hydrophilization performance, cell adhesion-inhibiting performance and biological sample adhesion-inhibiting performance, the repeating units (A-1), (A-2), (A-3), (A-4) and (A-6) are preferred, and the repeating units (A-1), (A-2), (A-3) and (A-6) are more preferred. Particularly, as the repeating unit (A), from the standpoint of attaining superior lubricity-imparting performance, hydrophilization performance, cell adhesion-inhibiting performance and biological sample adhesion-inhibiting performance, the following (i) and (ii) are preferred, and (ii) is particularly preferred.

(i) at least one selected from the repeating units (A-1) and (A-3), preferably the repeating unit (A-3)

(ii) a combination of at least one selected from the repeating units (A-1) and (A-3) and at least one selected from the repeating units (A-2) and (A-6), preferably a combination of (A-3) and at least one selected from the repeating units (A-2) and (A-6)

The total content of the repeating unit (A) is preferably 2.5 to 95% by mass, more preferably 5 to 95% by mass, still more preferably 20 to 95% by mass, yet still more preferably 30 to 95% by mass, particularly preferably 40 to 90% by mass, with respect to all repeating units of the above-described polymer.

When the total content of the repeating unit (A) is in this range, superior performance of imparting lubricity to a medical device, superior performance of hydrophilizing an equipment and inhibiting cell adhesion to the equipment, and superior performance of hydrophilizing a silicone substrate and inhibiting adhesion of a biological sample to the silicone substrate are attained.

The content of the repeating unit (A) can be measured by $^1$H-NMR, $^{13}$C-NMR or the like.

[Repeating Unit (B)]

The repeating unit (B) is a repeating unit which has a polyoxyalkylene group, and the terminal of the side chain is constituted by an alkyl group having 5 to 30 carbon atoms, an alkanoyl group having 5 to 30 carbon atoms, or an aryl group having 6 to 30 carbon atoms, and the polymer may have one, or two or more repeating units corresponding to the repeating unit (B).

By incorporating such a repeating unit (B) into the polymer: the adhesive strength of the polymer on a medical device, an equipment, an apparatus and a silicone substrate is increased and, because of the interaction between the repeating unit (B) and the repeating unit (A), a medical device having excellent lubricity and a medical device having excellent durability (sustainability of lubricity), particularly a medical device having excellent sustainability of lubricity even under friction that may be generated during the use thereof, can be easily obtained;

an equipment and an apparatus that have excellent surface hydrophilicity and cell adhesion-inhibiting effect, as well as a cell culture equipment having excellent sustainability of these effects, can be easily obtained; and a silicone substrate that has a hydrophilic surface and exhibits excellent properties of inhibiting adhesion of a sample component, particularly a biological sample, as well as a silicone substrate having excellent sustainability of these effects, can be easily obtained.

Therefore, even when the present composition is used for treating the surface of a microchannel, the polymer is unlikely to be detached by a gas, a liquid or the like that passes through the channel, so that a silicone substrate having a microchannel that exhibits desired effects over a long period of time can be obtained.

From the standpoints of ease of synthesis and the like, the repeating unit (B) is preferably a repeating unit derived from a monomer having an ethylenically unsaturated bond, or a repeating unit having a structure represented by the following Formula (b1) at a side chain terminal. Examples of the repeating unit having a structure represented by Formula (b1) at a side chain terminal include known repeating units, among which (meth)acrylate repeating units, (meth)acrylamide repeating units, and styrene repeating units are preferred. Particularly, a repeating unit represented by the following Formula (b2) is preferred.

(b1)

[wherein, $R^{32}$ represents an alkylene group having 2 to 4 carbon atoms; $R^{33}$ represents an alkyl group having 5 to 30 carbon atoms, an alkanoyl group having 5 to 30 carbon atoms, or an aryl group having 6 to 30 carbon atoms; and m represents 2 to 100 as an average value]

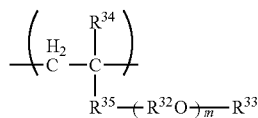

(b2)

[wherein, $R^{32}$, $R^{33}$ and m have the same meanings as in Formula (b1); $R^{34}$ represents a hydrogen atom or a methyl group; and $R^{35}$ represents —O—, —(C=O)—O—, —(C=O)—NR$^{36}$—, —NR$^{36}$—(C=O)— ($R^{36}$ represents a hydrogen atom or an organic group having 1 to 10 carbon atoms, and  represents a position at which the group is bound to the carbon atom bound with $R^{34}$ in Formula (b2)), or a phenylene group]

The number of carbon atoms of the alkylene group represented by $R^{32}$ is preferably 2 or 3, more preferably 2.

The alkylene group represented by $R^{32}$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Thereamong, from the standpoints of availability and the like, an ethane-1,2-diyl group is preferred.

It is noted here that m $R^{32}$s may be the same or different.

The numbers of carbon atoms of the alkyl group and alkanoyl group represented by $R^{33}$ are, from the standpoints of availability and the like, preferably 6 to 25, more preferably 7 to 20, still more preferably 8 to 18, yet still more preferably 9 to 18, particularly preferably 10 to 18.

The alkyl group represented by $R^{33}$ may be linear or branched, and specific examples thereof include a 2-ethylhexyl group, an octyl group, a decyl group, a lauryl group, a palmityl group, and a stearyl group. Thereamong, a 2-ethylhexyl group, a lauryl group and a stearyl group are preferred, and a lauryl group and a stearyl group are more preferred.

Examples of the alkanoyl group represented by $R^{33}$ include a 2-ethylhexanoyl group, a lauroyl group, and a stearoyl group.

The number of carbon atoms of the aryl group represented by $R^{33}$ is preferably 6 to 12. Specific examples thereof include a phenyl group.

The aryl group may also have an alkyl group having 1 to 24 carbon atoms as a substituent. The number of carbon atoms of this alkyl group is preferably 3 to 24, more preferably 5 to 16. The substitution position and the substitution number of the substituted alkyl group can be arbitrarily selected; however, the number of substitutions is preferably 1 or 2.

Examples of the aryl group that has such an alkyl group having 1 to 24 carbon atoms as a substituent include a nonylphenyl group.

Among these groups of $R^{33}$, from the standpoints of availability and the like, alkyl groups having 5 to 30 carbon atoms and aryl groups having 6 to 30 carbon atoms are preferred, and alkyl group having 5 to 30 carbon atoms are more preferred.

Examples of the phenylene group represented by $R^{35}$ include a 1,2-phenylene group, a 1,3-phenylene group, and a 1,4-phenylene group.

The number of carbon atoms of the organic group represented by $R^{36}$ is preferably 1 to 6. Examples of the organic group include hydrocarbon groups. Examples of the hydrocarbon groups include the same groups as those exemplified above for $R^5$.

Among the groups of $R^{35}$, —(C=O)—O— and a phenylene group are preferred, and —(C=O)—O— is particularly preferred.

The m is preferably 2 to 90, more preferably 4 to 90, still more preferably 9 to 60, particularly preferably 10 to 40, as an average value.

Examples of a monomer from which the repeating unit (B) is derived include 2-ethylhexylpolyethylene glycol (meth)acrylate, lauroxypolyethylene glycol (meth)acrylate, stearoxypolyethylene glycol (meth)acrylate, phenoxypolyethylene glycol (meth)acrylate, phenoxypolypropylene glycol (meth)acrylate, nonylphenoxypolypropylene glycol (meth)acrylate, 2-ethylhexylpolyethylene glycol polypropylene glycol (meth)acrylate, and nonylphenoxypolyethylene glycol polypropylene glycol (meth)acrylate, among which lauroxypolyethylene glycol (meth)acrylate and stearoxypolyethylene glycol (meth)acrylate are preferred.

The repeating unit (B) is, for example, a repeating unit obtained by using any one of these monomers individually, or two or more of the monomers.

The total content of the repeating unit (B) is preferably 2.5 to 95% by mass, more preferably 2.5 to 80% by mass, still more preferably 5 to 70% by mass, particularly preferably 5 to 60% by mass, with respect to all repeating units of the above-described polymer.

When the total content of the repeating unit (B) is in this range, since the polymer has superior lubricity-imparting performance, peeling resistance on a medical device and the like, superior hydrophilization performance and cell adhesion-inhibiting performance as well as superior hydrophilization performance and biological sample adhesion-inhibiting performance are attained.

It is noted here that the content of the repeating unit (B) may be measured in the same manner as the content of the repeating unit (A).

[Repeating Unit (C)]

The above-described polymer preferably contains at least one repeating unit (C) selected from a repeating unit (C-1) represented by the below-described Formula (c1) and a repeating unit (C-2) having a group represented by the below-described Formula (c2) at a side chain terminal.

By incorporating such a repeating unit (C) into the polymer:

the peeling resistance of the polymer on a medical device is further enhanced, and the lubricity-imparting effect is thus further improved;

the adhesive strength of the polymer on an equipment is further increased, and the hydrophilization performance and the cell adhesion-inhibiting performance are further improved; and the adhesive strength of the polymer on a silicone substrate is further increased, and the hydrophilization performance and the biological sample adhesion-inhibiting performance are further improved.

(Repeating Unit (C-1))

The repeating unit (C-1) is represented by the following Formula (c1):

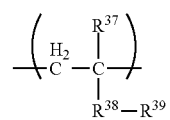

(c1)

[wherein, $R^{37}$ represents a hydrogen atom or a methyl group; $R^{38}$ represents —O—, *—(C=O)—O—, *—(C=O)—NR$^{40}$—, *—NR$^{40}$—(C=O)—($R^{40}$ represents a hydrogen atom or an organic group having 1 to 10 carbon atoms, and * represents a position at which the group is bound to the carbon atom bound with $R^{37}$ in Formula (c1)), or a phenylene group; and $R^{39}$ represents a hydrocarbon group having 4 to 30 carbon atoms].

Examples of the phenylene group represented by $R^{38}$ include a 1,2-phenylene group, a 1,3-phenylene group, and a 1,4-phenylene group.

The number of carbon atoms of the organic group represented by $R^{4o}$ is preferably 1 to 6. Examples of the organic group include hydrocarbon groups. Examples of the hydrocarbon groups include the same groups as those exemplified above for $R^5$.

Among the groups of $R^{38}$, from the standpoint of, for example, attaining excellent lubricity-imparting performance, hydrophilization performance, contamination resistance-imparting effect, cell adhesion-inhibiting performance, and biological sample adhesion-inhibiting performance, *—(C=O)—O—, *—(C=O)—NR$^{40}$—, and phenylene groups are preferred, *—(C=O)—O— and *—(C=O)—NR$^{40}$— are more preferred, *—(C=O)—O— and *—(C=O)—NH— are still more preferred, and ***—(C=O)—NH— is particularly preferred.

The hydrocarbon group represented by $R^{39}$ may be linear or branched and contain a cyclic structure, and the hydrocarbon group is preferably an alkyl group.

The number of carbon atoms of the hydrocarbon group represented by $R^{39}$ is, from the standpoint of, for example, attaining excellent lubricity-imparting performance, peeling resistance on a medical device, hydrophilization performance, cell adhesion-inhibiting performance and biological sample adhesion-inhibiting performance, preferably 6 to 24, more preferably 8 to 18, still more preferably 8 to 14, particularly preferably 10 to 14.

Examples of the above-described alkyl group include a 2-ethylhexyl group, an octyl group, a decyl group, a lauryl group, a palmityl group, and a stearyl group. Thereamong, from the standpoints of availability, contamination resistance-imparting effect and the like, a 2-ethylhexyl group, a lauryl group and a stearyl group are preferred, and a 2-ethylhexyl group and a lauryl group are more preferred.

Examples of a monomer from which the repeating unit (C-1) is derived include 2-ethylhexyl (meth)acrylate, lauryl (meth)acrylate, stearyl (meth)acrylate, and N-dodecyl (meth)acrylamide.

The repeating unit (C-1) is, for example, a repeating unit obtained by using any one of these monomers individually, or two or more of the monomers.

(Repeating Unit (C-2))

The repeating unit (C-2) is a repeating unit having a group represented by the following Formula (c2) at a side chain terminal. Examples of the repeating unit having a group represented by Formula (c2) at a side chain terminal include known repeating units, among which (meth)acrylate repeating units, (meth)acrylamide repeating units, and styrene repeating units are preferred. Particularly, a repeating unit represented by the following Formula (c3) is preferred.

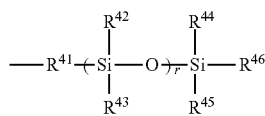

(c2)

[wherein, $R^{41}$ represents a divalent organic group having 1 to 10 carbon atoms; $R^{42}$ and $R^{43}$ each independently represent an organic group having 1 to 10 carbon atoms; $R^{44}$, $R^{45}$ and $R^{46}$ each independently represent —OSi($R^{49}$)$_3$ (each $R^{49}$ independently represents a hydrogen atom or an organic group having 1 to 8 carbon atoms), or an organic group having 1 to 10 carbon atoms; and r represents 0 to 200 as an average value]

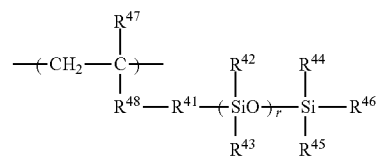

(c3)

[wherein, $R^{47}$ represents a hydrogen atom or a methyl group; $R^{48}$ represents —O—, *—(C=O)—O—, *—(C=O)—NR$^{50}$—, *—NR$^{50}$—(C=O)—($R^{50}$ represents a hydrogen atom or an organic group having 1 to 10 carbon atoms, and * represents a position at which the group is bound to the carbon atom bound with $R^{47}$ in Formula (c3)), or a phenylene group; and other symbols have the same meanings as in Formula (c2) 1

The number of carbon atoms of the divalent organic group represented by $R^{44}$ is preferably 2 to 8, more preferably 2 to 6, still more preferably 2 to 4.

The divalent organic group is, for example, a divalent hydrocarbon group. The divalent hydrocarbon group is preferably a divalent aliphatic hydrocarbon group and may be linear or branched, and the divalent hydrocarbon group is more preferably an alkanediyl group. Preferred specific examples of the alkanediyl group include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group.

The number of carbon atoms of the organic groups represented by $R^{42}$ and $R^{43}$ is preferably 1 to 6, more preferably 1 to 4, still more preferably 1 or 2.

The organic groups include hydrocarbon groups. The hydrocarbon groups may be linear or branched and are preferably alkyl groups. Specific examples of the alkyl groups include a methyl group, an ethyl group, an n-propyl group, an isopropyl group, an n-butyl group, an isobutyl group, a sec-butyl group, and a tert-butyl group.

When there are plural $R^{42}$s and $R^{43}$s, the plural $R^{42}$ may be the same or different, and the plural $R^{43}$ may also be the same or different.

The number of carbon atoms of the organic groups represented by $R^{44}$, $R^{45}$ and $R^{46}$ is preferably 1 to 6, more preferably 1 to 4, still more preferably 1 or 2. Examples of the organic groups represented by $R^{44}$, $R^{45}$, $R^{46}$ and $R^{49}$ include the same groups as those exemplified above for $R^{42}$ and $R^{43}$ From the standpoint of, for example, attaining excellent lubricity-imparting performance, peeling resistance on a medical device and hydrophilization performance, $R^{44}$, $R^{45}$ and $R^{46}$ are each preferably —OSi($R^{49}$)$_3$. Further, from the standpoint of, for example, attaining excellent lubricity-imparting performance, peeling resistance on a medical device and hydrophilization performance, $R^{49}$ is preferably an organic group having 1 to 8 carbon atoms, and the number of carbon atoms thereof is more preferably 1 to 6, still more preferably 1 to 4, particularly preferably 1 or 2.

From the standpoint of, for example, attaining excellent lubricity-imparting performance, peeling resistance on a medical device and hydrophilization performance, r is preferably 0 to 100, more preferably 0 to 50, still more preferably 0 to 25, particularly preferably 0 to 10, as an average value.

Examples of $R^{48}$ and $R^{50}$ include the same groups as those exemplified above for $R^{38}$ and $R^{40}$, respectively.

Examples of a monomer from which the repeating unit (C-2) is derived include 3-[tris(trimethylsiloxy)silyl]propyl (meth)acrylate, 3-[bis(trimethylsiloxy) (methyl)silyl]propyl (meth)acrylate, and silicone (meth)acrylate (e.g., X-22-2475 (manufactured by Shin-Etsu Chemical, Co. Ltd.) and FM-0711 (manufactured by JNC Corporation)).

The repeating unit (C-2) is, for example, a repeating unit obtained by using any one of these monomers individually, or two or more of the monomers.

Among these repeating units (C-1) and (C-2), from the standpoint of, for example, attaining excellent lubricity-imparting performance, peeling resistance on a medical device, hydrophilization performance, cell adhesion-inhibiting performance and biological sample adhesion-inhibiting performance, the repeating unit (C-1) wherein $R^{38}$ is ***—(C═O)—NH— and a repeating unit represented by Formula (c3) are preferred.

From the standpoint of, for example, attaining excellent lubricity-imparting performance, peeling resistance on a medical device, hydrophilization performance, cell adhesion-inhibiting performance and biological sample adhesion-inhibiting performance, the total content of the repeating unit (C) is preferably 40% by mass or less, more preferably 0.1 to 30% by mass, still more preferably 0.5 to 20% by mass, particularly preferably 1.0 to 10% by mass, with respect to all repeating units of the above-described polymer.

It is noted here that the content of the repeating unit (C) may be measured in the same manner as the content of the repeating unit (A).

[Repeating Unit (D) for Cross-Linking]

The polymer used in the present invention (I) may be cross-linked using a cross-linking agent. In cases where the repeating units (A) to (C) do not contain a reactive functional group reacting with the cross-linking agent or are weakly reactive and a cross-linking reaction does not proceed sufficiently, the polymer used in the present invention (I) may contain a repeating unit (D), which has a reactive functional group in a side chain, as a repeating unit other than the repeating units (A) to (C) within a range that does not impair the effects of the present invention (I).

By incorporating such a repeating unit (D) into the polymer and cross-linking the polymer on a medical device, the peeling resistance of the polymer (cross-linked polymer) on the medical device is further enhanced, and excellent lubricity-imparting effect is maintained for a longer period of time.

The reactive functional group is not particularly restricted; however, it is preferred to select a highly selective and reactive functional group such that, when the reactive functional group contained in the repeating unit (D) is cross-linked, a functional groups contained in the repeating units (A) to (C), such as a carboxyl group and a hydroxyl group, do not react at the same time. A preferred reactive functional group is variable depending on the repeating units selected as the repeating units (A) to (C), and examples thereof include an epoxy group, a carboxyl group, a hydroxyl group, an acid anhydride group, a ketone group, an aldehyde group, an isocyanate group, and an ethylenically unsaturated group. Thereamong, from the standpoints of the ease of introduction and the reactivity, the reactive functional group is preferably an epoxy group, a ketone group, or an ethylenically unsaturated group.

The repeating unit (D) can be introduced using a monomer having the above-described reactive functional group. In the monomer, the reactive functional group may be contained individually, or two or more thereof may be contained.

Specific examples of a monomer from which the repeating unit (D) is derived include monomers having an epoxy group in the molecule, such as glycidyl (meth)acrylate, methylglycidyl methacrylate, and allylglycidyl ether; monomers having an acid anhydride group in the molecule, such as maleic anhydride, itaconic anhydride, and citraconic anhydride; monomers having a ketone group in the molecule, such as diacetone acrylamide and acetoacetoxyethyl (meth)acrylate; monomers having an aldehyde group in the molecule, such as (meth)acrylaldehyde, crotonaldehyde, acrolein, and methacrolein; monomers having an isocyanate group in the molecule, such as (meth)acryloyloxymethyl isocyanate, (meth)acryloyloxyethyl isocyanate, (meth)acryloyloxypropyl isocyanate, and (meth)acryloyl isocyanate; and monomers having an ethylenically unsaturated group in the molecule, such as vinyl (meth)acrylate and allyl (meth)acrylate. The repeating unit (D) can be introduced using any one of these monomers individually, or two or more of the monomers.

Among these monomers, from the standpoints of the ease of introduction and the reactivity, glycidyl (meth)acrylate, diacetone acrylamide, and acetoacetoxyethyl methacrylate are preferred.

[Constitution, etc. of Polymer]

The mass ratio [(A):(B)] of the repeating units (A) and (B) contained in the polymer is, from the standpoint of, for example, attaining excellent lubricity-imparting performance, peeling resistance on a medical device, hydrophilization performance, cell adhesion-inhibiting performance and biological sample adhesion-inhibiting performance, preferably 20:80 to 95:5, more preferably 30:70 to 95:5, still more preferably 40:60 to 95:5, yet still more preferably 50:50 to 95:5, particularly preferably 55:45 to 95:5.

When the polymer has the repeating unit (C), from the standpoints of, for example, attaining excellent lubricity-imparting performance, peeling resistance on a medical device, hydrophilization performance, cell adhesion-inhibiting performance and biological sample adhesion-inhibiting performance and obtaining a cell culture equipment, a silicone substrate and the like that have excellent transparency, the mass ratio [((A)+(B)):(C)] is preferably 60:40 to 99:1, more preferably 70:30 to 99:1, still more preferably 75:25 to 99:1, yet still more preferably 80:20 to 99:1, particularly preferably 85:15 to 99:1.

It is particularly preferred that the mass ratio [(A):(B)] be in the above-described range of the mass ratio [(A):(B)] and the mass ratio [((A)+(B)):(C)] be in the above-described range of the mass ratio [((A)+(B)):(C)].

When the polymer has the repeating unit (D), the ratio between the repeating units (A), (B) and (C) and the repeating unit (D) is not particularly restricted; however, from the standpoint of improving the lubricity-imparting performance, peeling resistance on a medical device and cross-linking strength, the mass ratio [((A)+(B)+(C)):(D)] is preferably 50:50 to 99:1, more preferably 80:20 to 99:1, still more preferably 90:10 to 98:2.

The polymer may be any copolymer, which may be any of a block copolymer, a random copolymer and an alternating copolymer.

As for the weight-average molecular weight (Mw) of the polymer, the lower limit is preferably 3,000, more preferably 5,000, still more preferably 8,000, particularly preferably 10,000, and the upper limit is preferably 10,000,000, more preferably 5,000,000, still more preferably 3,000,000, particularly preferably 2,000,000. When the weight-average molecular weight is in this range, the lubricity-imparting effect, cell adhesion-inhibiting performance, biological sample adhesion-inhibiting performance, peeling resistance on a medical device, adsorptivity to an equipment, adsorptivity to a silicone substrate and ease of handling are improved.

As for the number-average molecular weight (Mn) of the polymer, the lower limit is preferably 2,000, more preferably 3,000, still more preferably 5,000, yet still more preferably 8,000, particularly preferably 10,000, and the upper limit is preferably 10,000,000, more preferably 5,000,000, still more preferably 3,000,000, yet still more preferably 2,000,000, particularly preferably 500,000.

Further, the molecular weight distribution (Mw/Mn) is preferably 1 to 10, more preferably 1 to 7, particularly preferably 1 to 5.

It is noted here that the weight-average molecular weight, the number-average molecular weight and the molecular weight distribution may be measured in accordance with the methods described below in Examples.

The polymer is preferably soluble in water. With the polymer being soluble in water:

a medical device having excellent lubricity can be easily produced without impairing the properties of the medical device;

a cell culture equipment and the like having excellent surface hydrophilicity and cell adhesion-inhibiting properties can be easily produced without impairing the properties of the equipment; and a silicone substrate having excellent surface hydrophilicity and biological sample adhesion-inhibiting properties can be easily produced without impairing the properties of the silicone substrate.

In the present specification, a polymer that is "soluble in water" refers to a polymer which yields a visually transparent solution when the polymer is added to and mixed with water (25° C.) such that the resultant has a polymer concentration of 0.5% by mass.

The polymer can be obtained by, for example, mixing the monomers from which the respective repeating units are derived, dissolving the resulting mixture in a solvent (e.g., water, acetonitrile or t-butyl alcohol) as required, and then performing radical polymerization of the resultant with an addition of a polymerization initiator.

The polymerization initiator used for performing the radical polymerization is not particularly restricted as long as it is an ordinary radical polymerization initiator, and examples thereof include benzoyl peroxide, lauroyl peroxide, diisopropyl peroxydicarbonate, t-butyl peroxy-2-ethylhexanoate, t-butyl peroxypivalate, t-butyl peroxydiisobutyrate, azobis-isobutyronitrile, azobis-isodimethylvaleronitrile, persulfates, and persulfate-bisulfites.

The polymerization initiator is added in an amount of preferably 0.001 to 10 parts by mass, more preferably 0.01 to 5 parts by mass, with respect to 100 parts by mass of the monomer components. Further, the polymerization temperature is preferably 20 to 100° C., and the polymerization time is preferably 0.5 to 48 hours.

<Present Composition>

The above-described medical device composition and silicone substrate treatment composition are not particularly restricted as long as they contain the above-described polymer, and these compositions usually contain a component (s) other than the polymer, such as a solvent. Further, the above-described cell adhesion inhibitor is also not particularly restricted as long as it contains the above-described polymer, and the cell adhesion inhibitor may also contain a component (s) other than the polymer, such as a solvent, within a range that does not impair the effects of the present invention.

These present compositions can be produced in accordance with a conventional method.

The content of the polymer in each present composition is preferably 0.001 to 20° by mass, more preferably 0.01 to 10° by mass, still more preferably 0.01 to 5% by mass.

With the content of the polymer being in this range:

a medical device which has excellent lubricity and maintains its effects can be easily obtained;

a cell culture equipment which exhibits excellent hydrophilization performance and cell adhesion-inhibiting performance and has low cytotoxicity can be easily obtained; and a silicone substrate, particularly a silicone substrate which has excellent hydrophilization performance and biological sample adhesion-inhibiting properties can be easily treated with the composition.

As the above-described other component(s), for example, a solvent, a surfactant, an isotonizing agent, a chelating agent, a pH modifier, a buffer, a thickening agent, a stabilizer, a protease, a pharmacologically active component, a physiologically active component, and the various additives described in Japanese Pharmaceutical Excipients Directory 2007 (edited by the International Pharmaceutical Excipients Council Japan) may be incorporated within a range that does not impair the effects of the present invention. These components may be used individually or two or more thereof.

Examples of the solvent include water; and various aqueous buffer solutions, such as phosphate buffer, glycine buffer, Good's buffer, Tris buffer, and ammonia buffer.

Examples of the surfactant include amphoteric surfactants, such as alkyldiaminoethylglycines and salts thereof (e.g., hydrochlorides); cationic surfactants, such as benzalkonium chloride and benzethonium chloride; and anionic surfactants, such as alkyl benzenesulfonates, alkyl sulfates, polyoxyethylene alkyl sulfates, aliphatic α-sulfomethyl esters, and α-olefin sulfonates.

Examples of the isotonizing agent include disodium hydrogen phosphate, sodium dihydrogen phosphate, potassium dihydrogen phosphate, sodium hydrogen sulfite, sodium sulfite, potassium chloride, calcium chloride, sodium chloride, magnesium chloride, potassium acetate, sodium acetate, sodium bicarbonate, sodium carbonate, sodium thiosulfate, magnesium sulfate, glycerin, and propylene glycol.

Examples of the chelating agent include ethylenediaminetetraacetic acid (EDTA); salts of ethylenediaminetetraacetic acid, such as disodium ethylenediaminetetraacetate (EDTA-2Na) and trisodium ethylenediaminetetraacetate (EDTA-3Na); and citric acid, gluconic acid, tartaric acid, and salts thereof (e.g., sodium salts).

Examples of the pH modifier include hydrochloric acid, boric acid, ε-aminocaproic acid, citric acid, acetic acid, sodium hydroxide, potassium hydroxide, calcium hydroxide, magnesium hydroxide, sodium bicarbonate, sodium carbonate, borax, triethanolamine, monoethanolamine, diisopropanolamine, sulfuric acid, phosphoric acid, polyphosphoric acid, propionic acid, oxalic acid, gluconic acid, fumaric acid, lactic acid, tartaric acid, malic acid, succinic acid, gluconolactone, and ammonium acetate.

The pH modifier may be used such that the pH value of the solution is adjusted to be 4.0 to 9.0 or so, preferably 6.0 to 8.0 or so, more preferably about 7.0.

Examples of the buffer include citric acid, malic acid, lactic acid, ascorbic acid, maleic acid, gluconic acid, phosphoric acid, boric acid, oxycarboxylic acid, amino acids (e.g., glycine and glutamic acid), tris(hydroxymethyl)aminomethane (Tris) and salts thereof (e.g., sodium salts), Good's buffer containing taurine or a derivative thereof, and hydroxyalkylamines (e.g., bis(2-hydroxyethyl)iminotris(hydroxymethyl)methane (Bis-tris).

Examples of the thickening agent and the stabilizer include synthetic organic polymer compounds, such as polyvinyl alcohols, poly-N-vinylpyrrolidones, polyethylene glycols, polypropylene glycols, and polyacrylamides; cellulose derivatives, such as hydroxyethyl cellulose, hydroxypropyl cellulose, and hydroxypropylmethyl cellulose; starch derivatives, such as sodium carboxymethyl starch and hydroxyethyl starch; and chondroitin sulfate, and hyaluronic acid salts.

Examples of the protease include biologically derived proteases, such as papain, bromelain, ficin, trypsin, chymotrypsin, and pancreatin.

When the above-described polymer is cross-linked, the medical device composition may also contain a cross-linking agent, such as a polyfunctional compound capable of reacting with a functional group contained in the repeating units (A) to (C), a reactive functional group of the repeating unit (D) or the like, and/or a polymerization initiator.

Examples of the polyfunctional compound include polyols, polyfunctional amines, polyfunctional thiols, polyfunctional isocyanates, hydrazide compounds, and polyfunctional ethylenically unsaturated compounds. These polyfunctional compounds may be used individually or two or more thereof.

Examples of the polyols include dihydric alcohols having 2 to 20 carbon atoms (aliphatic diols [e.g., alkylene glycols, such as ethylene glycol, propylene glycol, 1,3- or 1,4-butanediol, 1,6-hexanediol, and neopentyl glycol], and alicyclic diols [e.g., cycloalkylene glycols, such as cyclohexanediol and cyclohexane dimethanol]); trihydric alcohols having 3 to 20 carbon atoms (aliphatic triol, for example, alkane triols, such as glycerin, trimethylolpropane, trimethylolethane, and hexanetriol); and tetrahydric to octahydric, or higher hydric alcohols having 5 to 20 carbon atoms (aliphatic polyols [e.g., alkane polyols, such as pentaerythritol, sorbitol, mannitol, sorbitan, diglycerin, and dipentaerythritol], intramolecular or intermolecular dehydration products of alkane triols or alkane polyols, and saccharides and derivatives thereof [e.g., sucrose, glucose, mannose, fructose, and methyl glucoside]).

Examples of the polyfunctional amines include ethylenediamine, propylenediamine, hexamethylenediamine, dialkylenetriamines, trialkylenetetramines, tetraalkylenepentamines, pentaalkylenehexamines, and hexaalkyleneheptamines.

Examples of the polyfunctional thiols include ethylene dithiol, 1,6-hexane dithiol, and 3,6-dioxa-1,8-octane dithiol.

Examples of the polyfunctional isocyanates include 1,6-hexamethylene diisocyanate, 2,2,4-trimethylhexamethylene diisocyanate, lysine diisocyanate, isophorone diisocyanate, 4,4'-dicyclohexylmethane diisocyanate, 1,4-cyclohexane diisocyanate, norbornane diisocyanate, 1,3- or 1,4-phenylene diisocyanate, 2,4- or 2,6-tolylene diisocyanate, and 2,4'- or 4,4'-diphenylmethane diisocyanate.

Examples of the hydrazide compounds include oxalic acid dihydrazide, malonic acid dihydrazide, succinic acid dihydrazide, glutaric acid dihydrazide, adipic acid dihydrazide, sebacic acid dihydrazide, phthalic acid dihydrazide, isophthalic acid dihydrazide, terephthalic acid dihydrazide, maleic acid dihydrazide, fumaric acid dihydrazide, itaconic acid dihydrazide, citric acid trihydrazide, nitriloacetic acid trihydrazide, cyclohexane tricarboxylic acid trihydrazide, ethylenediaminetetraacetic acid tetrahydrazide, ethylene-1,2-dihydrazine, propylene-1,2-dihydrazine, propylene-1,3-dihydrazine, butylene-1,2-dihydrazine, butylene-1,3-dihydrazine, butylene-1,4-dihydrazine, and butylene-2,3-dihydrazine.

Examples of the polyfunctional ethylenically unsaturated compounds include ethylene glycol di(meth)acrylate, diethylene glycol di(meth)acrylate, triethylene glycol di(meth)acrylate, polyethylene glycol di(meth)acrylate, 1,3-butylene glycol di(meth)acrylate, 1,6-hexanediol di(meth)acrylate, neopentyl glycol di(meth)acrylate, polypropylene glycol di(meth)acrylate, 2,2-bis[4-((meth)acryloxyethoxy)phenyl] propane, 2-hydroxy-1-acryloxy-3-methacryloxy propane, trimethylolpropane tri(meth)acrylate, trimethylolpropane tetra(meth)acrylate, tetramethylolmethane tri(meth)acrylate, tetramethylolmethane tetra(meth)acrylate, ditrimethylolpropane tetra(meth)acrylate, triallyl cyanurate, and triallyl isocyanurate.

When the medical device composition contains a compound having an ethylenically unsaturated group, a polymerization initiator may be used and, as the polymerization initiator, any known photopolymerization initiator or thermal polymerization initiator can be used.

Such a polymerization initiator may be used individually, or two or more thereof may be used.

Examples of the photopolymerization initiator include thioxanthone compounds, acetophenone compounds, benzyl compounds, biimidazole compounds, triazine compounds, o-acyloxime compounds, onium salt compounds, benzoin compounds, benzophenone compounds, α-diketone compounds, polynuclear quinone compounds, diazo compounds, and imide sulfonate compound.

Specific examples include 2,2-diethoxyacetophenone, 4'-isopropyl-2-hydroxy-2-methyl-propiophenone, 2-hydroxy-2-methyl-propiophenone, p-dimethylaminoacetone, p-Cert-butyldichloroacetophenone, p-tert-butyltrichloroacetophenone, p-azidobenzalacetophenone, benzyl, benzyldimethyl ketal, benzyl-β-methoxyethyl acetal, 1-hydroxycyclohexyl phenyl ketone, benzoin, benzoin methyl ether, benzoin ethyl ether, benzoin-n-propyl ether, benzoin isopropyl ether, benzoin-n-butyl ether, benzoin isobutyl ether, benzophenone, methyl o-benzoylbenzoate, Micheler's ketone, 4,4'-bis-diethylaminobenzophenone, 4,4'-dichlorobenzophenone, thioxanthone, 2-methylthioxanthone, 2-ethylthioxanthone, 2-isopropylthioxanthone, 4-isopropylthioxanthone, 2-chlorothioxanthone, and 2,4-diethylthioxanthone.

Examples of the thermal polymerization initiator include the same initiators as the radical polymerization initiators that may be used in the synthesis of the above-described polymer.

<Medical Device>

The medical device is not particularly restricted as long as it is a medical equipment, and specific examples thereof include blood bags, urine collection bags, blood transfusion sets, surgical sutures, drain tubes, various catheters, blood accesses, blood circuits, artificial blood vessels, artificial kidneys, artificial heart and lungs, prosthetic valves, plasmapheresis membranes, various adsorbents, CAPDs, IABPs, pacemakers, prostheses, artificial femoral heads, dental materials, and various shunts.

The material and the shape of the medical device are not particularly restricted, and examples of the material include various polymeric materials, such as polyolefins, modified polyolefins, polyethers, polyurethanes, polyamides, polyimides, polyesters (e.g., polyethylene terephthalate), polytetrafluoroethylenes, polyvinyl chlorides, and copolymers thereof; metals; ceramics; carbon; and composite materials thereof. The shape is not particularly restricted, and the medical device may be, for example, smooth or porous.

<Silicone Substrate>

The silicone substrate to be treated with the above-described silicone substrate treatment composition is not particularly restricted as long as it is a substrate containing a silicone resin. Specific examples of such a silicone substrate include silicone-containing medical devices, silicone substrates having a microchannel, preferably silicone-containing microchannel devices.

These medical devices refer to medical structures used in a living body, and such structures are generally classified into those which are implanted in a body and those which are used in a body (without implantation). The size and the length of the medical devices are not particularly restricted, and the medical devices encompass those having a microcircuit and those for detecting a trace amount of a sample.

Examples of the structures which are implanted in a body include function-supporting apparatuses for covering a function of a living body suffering from a disease, such as cardiac peacemakers; apparatuses for detecting abnormality in a living body, such as implantable biochips; and medical tools such as implants, bone fixation materials, surgical sutures, and artificial blood vessels.

Examples of the structures which are used in a body (without implantation) include catheters and gastroscopes.

Examples of the microchannel devices include microanalysis devices, such as microreaction devices (specifically, microreactors, microplants and the like), integrated nucleic acid analysis devices, micro electrophoresis devices, and micro chromatography devices; micro devices for preparation of samples for analysis such as mass spectrometry or liquid chromatography; physicochemical treatment devices used for extraction, membrane separation, dialysis and the like; and microchannel chips, such as environmental analysis chips, clinical analysis chips, gene analysis chips (DNA chips), protein analysis chips (proteome chips), sugar-chain chips, chromatographic chips, cell analysis chips, and drug screening chips. Thereamong, microchannel chips are preferred.

The microchannel is a part through which a trace amount of a sample (preferably a liquid sample) flows, and the width and the depth of the microchannel is not particularly restricted; however, they are both usually 0.1 µm to 1 mm or so, preferably 10 µm to 800 µm.

The width and the depth of the microchannel may be the same over the entire channel length, or the microchannel may partially vary in size and/or shape.

The silicone substrate may be subjected to, for example, a plasma treatment, a UV-ozone treatment, or a treatment with an internal wetting agent. The silicone substrate subjected to any of such treatments has a hydrophilized surface, making a polymer unlikely to adsorb thereto in some cases; however, the polymer used in the present invention also adsorbs to such a silicone substrate subjected to a plasma treatment or the like, and the silicone substrate is thereby imparted with excellent hydrophilicity and excellent biological sample adsorption-inhibiting effect.

<<Article>>

The article of the present invention is selected from the group consisting of a medical device, a cell culture equipment and a silicone substrate, and comprises a polymer having the following repeating units (A) and (B) on at least a part of the surface:

(A) a hydrophilic repeating unit; and (B) a repeating unit which has a polyoxyalkylene group in a side chain whose terminal is constituted by an alkyl group having 5 to 30 carbon atoms, an alkanoyl group having 5 to 30 carbon atoms, or an aryl group having 6 to 30 carbon atoms.

<<Medical Device Comprising Polymer or Cross-Linked Product of Polymer on Surface>>

The medical device comprising a polymer or a cross-linked product of a polymer on the surface according to the present invention (hereinafter, referred to as "treatment subject 1") comprises the above-described polymer or a cross-linked product thereof on at least a part of the medical device surface.

The treatment subject 1 comprises, on its surface, the above-described polymer or a cross-linked product thereof, and thus has excellent lubricity.

The treatment subject 1 can be produced by a method comprising a step of arranging, specifically coating, the polymer on at least a part of the medical device surface.

Alternatively, the treatment subject 1 may be produced by a method comprising a step of arranging a cross-linked product of the polymer on at least a part of the medical device surface, specifically a step of coating the medical device surface with a cross-linked product of the polymer; however, from the standpoints of, for example, further enhancing the peeling resistance of the polymer (cross-linked polymer) on the medical device and maintaining excellent lubricity-imparting effect over a longer period of time, it is preferred to produce the treatment subject 1 by a method comprising the steps of: arranging (e.g., coating) the polymer on at least a part of the medical device surface; and subsequently cross-linking the polymer.

The coating may be performed using the above-described medical device composition or only the polymer; however, it is preferred to use the medical device composition since the treatment subject 1 can thereby be easily obtained.

The medical device prior to the treatment may be subjected to a surface treatment such as a plasma treatment or a UV-ozone treatment in advance.

The coating may be performed by a known method, and specific examples thereof include spray coating, dip coating, flow coating, brush coating, and sponge coating. In addition, the coating can also be performed by simply immersing the medical device in the above-described medical device composition or the like and thereby bringing the medical device into contact with the polymer or a cross-linked product of the polymer.

During the coating, it is preferred to perform heating with the medical device composition and the medical device being in contact with each other since this enables to produce the treatment subject 1 having excellent lubricity, particularly the treatment subject 1 exhibiting its effects over a long period of time, in a simple and low-cost manner.

As for the conditions of the heating, the temperature is preferably 30 to 150° C., more preferably 30 to 135° C., still more preferably 35 to 135° C., and the heating time is preferably 20 minutes to 72 hours, more preferably 20 minutes to 24 hours. The heating conditions may be determined in accordance with the medical device and polymer to be used. Further, when the temperature is low, the heating time may be selected in accordance with the heating temperature by, for example, extending the heating time, or the heating temperature may be selected in accordance with the heating time.

More specifically, the heating may be performed under either the below-described normal pressure conditions or sterilization conditions, or under a combination of these conditions.

The normal pressure conditions are preferably 30 minutes to 72 hours at 30 to 80° C. under normal pressure, more preferably 1 hour to 24 hours at 35 to 70° C. under normal pressure, still more preferably 1 hour to 24 hours at 35 to 60° C. under normal pressure.

The heating under the sterilization conditions may be performed at the time of autoclave sterilization or the like of the medical device and, in this case, the sterilization conditions are preferably in a range of 30 minutes at 115° C. to 20 minutes at 135° C., more preferably 30 minutes at 120° C. to 20 minutes at 135° C.

The term "autoclave sterilization" used herein refers to the high-pressure steam sterilization method described in the Japanese Pharmacopoeia 16th Edition, and the autoclave sterilization can be performed under the same conditions as the general example described in the Japanese Pharmacopoeia 16th Edition, or for a longer period of time.

The step of cross-linking the polymer can be performed by a known method. For example, after coating a composition containing the above-described polymer and polyfunctional compound, the thus coated composition is treated with heat and/or light, whereby the strength and the durability of the resulting coating layer can be largely improved. It is noted here that the composition can also be cured using a cross-linking agent.

For example, when the polymer contains the repeating unit (D) having a ketone group, a composition which contains the polymer and a dihydrazide compound (e.g., adipic acid dihydrazide) as the polyfunctional compound is prepared, and a medical device is immersed in this composition and then taken out, after which the resultant is heated and dried, whereby covalent bonds can be formed between the ketone group and the hydrazide groups, and the polymer can thus be firmly immobilized on the medical device surface without impairing the properties provided by the polymer. It is preferred that 10 to 100% of the total amount of the ketone group contained in the composition undergo a hydrazonation reaction with the hydrazide groups of the polyfunctional compound. Further, when the polymer contains the repeating unit (D) having an epoxy group, a composition which contains the polymer and a dithiol compound (e.g., 3,6-dioxa-1,8-octanedithiol) or a diamine compound (e.g., ethylenediamine) as the polyfunctional compound is prepared, and a medical device is immersed in this composition and then taken out, after which the resultant is heated, whereby covalent bonds can be formed between the epoxy group and the thiol groups or the amino groups, so that the same effect as described above can be exerted.

The treatment subject 1 may be produced in the same manner as an ordinary surface treatment method except for the above-described steps and, for example, a washing step and a drying step may also be performed as required after the above-described steps.

<<Cell Culture Equipment>>

The cell culture equipment of the present invention comprises the above-described polymer on at least a part of the surface. Specifically, the polymer is coated on at least a part of the cell culture equipment.

Further, the cell culture equipment of the present invention is preferably an equipment whose surface is hydrophilically modified by the formation of a hydrophilic layer thereon and thus has a cell adhesion-inhibiting effect.

<<Method of Producing Cell Culture Equipment>>

The cell culture equipment can be produced by a method comprising a step of arranging the polymer on at least a part of the equipment surface, specifically a method comprising a step of coating the equipment surface with the polymer. The cell culture equipment may be produced in the same manner as an ordinary cell culture equipment production method except for the coating. The coating may be performed using the above-described cell adhesion inhibitor or only the polymer; however, it is preferred to use the cell adhesion inhibitor since the cell culture equipment can thereby be easily obtained.

Examples of the equipment include a flask, a tissue culture flask, a dish, a Petri dish, a tissue culture dish, a multi-dish, a microplate, a microwell plate, a micropore, a multi-plate, a multi-well plate, a chamber slide, a schale, a tube, a tray, a culture bag, and a roller bottle.

The coating may be performed by a known method, and specific examples thereof include the same methods as those described above in the section of the medical device. In addition, the coating can also be performed by immersing the equipment in the above-described cell adhesion inhibitor or the like and thereby bringing the equipment into contact with the polymer.

During the coating, it is preferred to perform heating with the cell adhesion inhibitor and the equipment being in contact with each other since this enables to produce a cell culture equipment having excellent hydrophilicity and excellent cell adhesion-inhibiting properties, particularly a cell culture equipment exhibiting these effects over a long period of time, in a simple and low-cost manner.

Examples of the conditions of the heating include the same conditions as those described above in the section of the medical device, and a preferred range thereof is also the same as described above.

The cell culture equipment may be produced in the same manner as an ordinary surface treatment method except for the step of arranging the polymer and, for example, a washing step and a drying step may also be performed as required after the above-described steps, and a plasma treatment, a UV-ozone treatment or the like may also be performed before the step of arranging the polymer.

Further, a step of curing the polymer using a cross-linking agent or a cross-linking monomer may also be incorporated.

<<Method of Producing Cell Cluster>>

The method of producing a cell cluster according to the present invention is characterized by comprising culturing cells using the above-described cell culture equipment.

Since the polymer is arranged on the surface of the cell culture equipment, adhesion of cells to the equipment is suppressed. Thus, by culturing cells in this equipment, the cells adhere only between themselves, so that a cell cluster can be obtained. Particularly, since the formation of a cell cluster is unlikely to be inhibited because of the low cytotoxicity of the cell culture equipment, a cell cluster can be easily obtained. It is desired that the time required for obtaining a cell cluster be preferably 24 hours or less, more preferably 12 hours or less.

As the cell culturing conditions in this process, culturing conditions suitable for the cells to be used may be employed as appropriate.

<<Silicone Substrate Comprising Polymer on Surface and Silicone Substrate Having Microchannel>>

The silicone substrate comprising a polymer on the surface and the silicone substrate having a microchannel according to the present invention (hereinafter, these silicone substrates are collectively referred to as "treatment subject 2") comprise the above-described polymer on at least a part of the surface of a substrate, namely a silicone substrate and a silicone substrate having a microchannel, respectively.

The treatment subject 2 has the polymer on its surface; therefore, the treatment subject 2 exhibits excellent hydrophilicity and excellent effect of inhibiting adsorption of a sample component, particularly a biological sample.

In the case of a silicone substrate having a microchannel, the term "surface of a substrate" refers to, for example, a surface of the silicone substrate or an inner surface of the microchannel. That is, a silicone substrate having a microchannel which comprises a polymer on the surface may have the above-described polymer on the surface of the substrate or on the surface of the microchannel; however, it is preferred that the silicone substrate have the polymer at least on the surface of the microchannel since the effects of the present invention are thereby more prominently exhibited.

The treatment subject 2 can be produced by a method comprising a step of arranging, specifically coating, the polymer on at least a part of the surface of a silicone substrate or a silicone substrate having a microchannel. The coating may be performed using the above-described silicone substrate treatment composition or only the polymer; however, it is preferred to use the silicone substrate treatment composition since the treatment subject 2 can thereby be easily obtained.

The coating may be performed by a known method, and specific examples thereof include the same methods as those described above in the section of the medical device. In addition, the coating can also be performed by simply immersing the silicone substrate or the silicone substrate having a microchannel in the above-described silicone substrate treatment composition or the like and thereby bringing the substrate into contact with the polymer. Particularly, it is usually not easy to coat an inner surface of the microchannel due to the size of the diameter and the like; however, according to the above-described silicone substrate treatment composition which comprises the specific polymer, the surface of the microchannel can be coated simply by bringing the polymer into contact with the substrate, so that the desired treatment subject 2 can be obtained easily and inexpensively.

It is noted here that the coating of the microchannel is preferably performed on substantially the entire surface (including the entire surface) of the channel.

During the coating, it is preferred to perform heating with the silicone substrate treatment composition and the substrate being in contact with each other since this enables to produce the treatment subject 2 which exhibits excellent hydrophilicity and excellent effect of inhibiting adsorption of a sample component, particularly a biological sample, especially the treatment subject 2 exhibiting these effects over a long period of time, in a simple and low-cost manner.

Examples of the conditions of the heating include the same conditions as those described above in the section of the medical device, and a preferred range thereof is also the same as described above.

The treatment subject 2 may be produced in the same manner as an ordinary surface treatment method except for the above-described steps and, for example, a washing step and a drying step may also be performed as required after the above-described steps.

Further, a step of curing the polymer using a cross-linking agent or a cross-linking monomer may also be incorporated.

EXAMPLES

The present invention will now be described in detail by way of examples thereof; however, the present invention is not restricted to the following examples.

The conditions of each analysis were as follows.

<Measurement of Molecular Weight>

The weight-average molecular weight (Mw) and the number-average molecular weight (Mn) were measured by gel permeation chromatography (GPC) based on a polystyrene standard, using a TSKgel α-M column manufactured by Tosoh Corporation under the following analysis conditions: flow rate=0.5 mL/min, elution solvent=N-methyl-2-pyrrolidone solvent ($H_3PO_4$: 0.016 M, LiBr: 0.030 M), and column temperature=40° C.

<NMR Spectrum>

The structures (repeating unit contents) of the copolymers obtained below were each determined based on $^1$H-NMR spectrum.

The $^1$H-NMR spectrum was measured by Model AVANCE 500 (500 MHz) manufactured by Bruker Corp. using $d_6$-DMSO as a solvent and an internal standard substance.

Synthesis Example 1

Synthesis of Copolymer (N-1)

In a flask, 8.5 g of methoxypolyethylene glycol (23) monomethacrylate (M-230 G (manufactured by Shin-Nakamura Chemical Co., Ltd.); hereinafter, referred to as "MPEGM". It is noted here that "polyethylene glycol (23)" means "$(OC_2H_4)_{23}$", and the same applies hereinbelow), 0.25 g of NHmethacryloyloxyethyl-N,N-dimethylammonium-α-N-methylcarboxy betaine (GLBT (manufactured by Osaka Organic Chemical Industry Ltd.); hereinafter, referred to as "GLBT"), 1.25 g of lauroxypolyethylene glycol (30) monomethacrylate (PLE-1300 (manufactured by NOF Corporation); hereinafter, referred to as "LPEGM"), 0.1 g of 2,2'-azobis(isobutyronitrile) (manufactured by Wako Pure Chemical Industries, Ltd.; hereinafter, referred to as "AIBN") as a polymerization initiator, and 27 g of pure water and 63 g of acetonitrile as a solvent were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-1) was obtained.

In the thus obtained copolymer (N-1), the content of an MPEGM-derived repeating unit was 85% by mass; the content of a GLBT-derived repeating unit was 2.5% by mass; and the content of an LPEGM-derived repeating unit was 12.5% by mass.

Further, the thus obtained copolymer (N-1) had a weight-average molecular weight of 235,000, a number-average molecular weight of 58,000, and a molecular weight distribution of 4.1.

Synthesis Example 2

Synthesis of Copolymer (N-2)

In a flask, 8.5 g of acryloyl morpholine (ACMO (manufactured by KJ Chemicals Corporation); hereinafter, referred to as "ACM"), 0.25 g of GLBT, 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-2) was obtained.

In the thus obtained copolymer (N-2), the content of an ACM-derived repeating unit was 85° by mass; the content of a GLBT-derived repeating unit was 2.5% by mass; and the content of an LPEGM-derived repeating unit was 12.5% by mass.

Further, the thus obtained copolymer (N-2) had a weight-average molecular weight of 455,000, a number-average molecular weight of 137,000, and a molecular weight distribution of 3.3.

Synthesis Example 3

Synthesis of Copolymer (N-3)

In a flask, 8.5 g of dimethylacrylamide (DMAA (manufactured by KJ Chemicals Corporation); hereinafter, referred to as "DMA"), 0.25 g of GLBT, 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-3) was obtained.

In the thus obtained copolymer (N-3), the content of a DMA-derived repeating unit was 85% by mass; the content of a GLBT-derived repeating unit was 2.5° by mass; and the content of an LPEGM-derived repeating unit was 12.5° by mass.

Further, the thus obtained copolymer (N-3) had a weight-average molecular weight of 499,000, a number-average molecular weight of 125,000, and a molecular weight distribution of 4.0.

Synthesis Example 4

Synthesis of Copolymer (N-4)

In a flask, 8.5 g of N-vinylpyrrolidone ((manufactured by Wako Pure Chemical Industries, Ltd.); hereinafter, referred to as "NVP"), 0.25 g of GLBT, 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-4) was obtained.

In the thus obtained copolymer (N-4), the content of an NVP-derived repeating unit was 85% by mass; the content of a GLBT-derived repeating unit was 2.5% by mass; and the content of an LPEGM-derived repeating unit was 12.5% by mass.

Further, the thus obtained copolymer (N-4) had a weight-average molecular weight of 208,000, a number-average molecular weight of 43,000, and a molecular weight distribution of 4.8.

Synthesis Example 5

Synthesis of Copolymer (N-5)

In a flask, 8.5 g of DMA, 0.25 g of 2-methacryloyloxy-ethyl phosphorylcholine ((manufactured by Tokyo Chemical Industry Co., Ltd.); hereinafter, referred to as "MPC"), 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-5) was obtained.

In the thus obtained copolymer (N-5), the content of a DMA-derived repeating unit was 85% by mass; the content of an MPC-derived repeating unit was 2.5% by mass; and the content of an LPEGM-derived repeating unit was 12.5% by mass.

Further, the thus obtained copolymer (N-5) had a weight-average molecular weight of 494,000, a number-average molecular weight of 153,000, and a molecular weight distribution of 3.2.

Synthesis Example 6

Synthesis of Copolymer (N-6)

In a flask, 8.5 g of DMA, 0.25 g of acrylic acid (manufactured by Nippon Shokubai Co., Ltd.; hereinafter, referred to as "AA"), 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. 0.31 g of sodium bicarbonate was dissolved by adding the thus obtained solution, and the resultant was dialyzed with pure water, whereby an aqueous solution of a copolymer (N-6) was obtained.

In the thus obtained copolymer (N-6), the content of a DMA-derived repeating unit was 85% by mass; the content of an AA-derived repeating unit was 2.5% by mass; and the content of an LPEGM-derived repeating unit was 12.5% by mass.

Further, the thus obtained copolymer (N-6) had a weight-average molecular weight of 436,000, a number-average molecular weight of 103,000, and a molecular weight distribution of 4.2.

Synthesis Example 7

Synthesis of Copolymer (N-7)

In a flask, 8.5 g of DMA, 0.25 g of dimethylaminopropylacrylamide methyl chloride quaternary salt (DMAPAA-Q (manufactured by KJ Chemicals Corporation); hereinafter, referred to as "QA"), 1.25 g of LPEGM, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-7) was obtained.

In the thus obtained copolymer (N-7), the content of a DMA-derived repeating unit was 85% by mass; the content of a QA-derived repeating unit was 2.5% by mass; and the content of an LPEGM-derived repeating unit was 12.5% by mass.

Further, the thus obtained copolymer (N-7) had a weight-average molecular weight of 549,000, a number-average molecular weight of 172,000, and a molecular weight distribution of 3.2.

Synthesis Example 8

Synthesis of Copolymer (N-8)

In a flask, 8.75 g of MPC, 1.25 g of LPEGM, 0.1 g of AIBN, and 90 g of t-butanol (manufactured by Wako Pure Chemical Industries, Ltd.; hereinafter referred to as "TBA") were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-8) was obtained.

In the thus obtained copolymer (N-8), the content of an MPC-derived repeating unit was 87.5% by mass, and the content of an LPEGM-derived repeating unit was 12.5% by mass.

Further, the thus obtained copolymer (N-8) had a weight-average molecular weight of 153,000, a number-average molecular weight of 39,000, and a molecular weight distribution of 3.9.

[Synthesis Example 9] Synthesis of Copolymer (N-9)

In a flask, 8.75 g of GLBT, 1.25 g of LPEGM, 0.1 g of AIBN, and 90 g of TBA were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-9) was obtained.

In the thus obtained copolymer (N-9), the content of a GLBT-derived repeating unit was 87.5° by mass, and the content of an LPEGM-derived repeating unit was 12.5° by mass.

Further, the thus obtained copolymer (N-9) had a weight-average molecular weight of 197,000, a number-average molecular weight of 44,000, and a molecular weight distribution of 4.5.

Synthesis Example 10

Synthesis of Copolymer (N-10)

In a flask, 8.5 g of DMA, 0.25 g of GLBT, 1.25 g of stearoxypolyethylene glycol (30) monomethacrylate (PSE-1300 (manufactured by NOF Corporation); hereinafter, referred to as "SPEGM"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-10) was obtained.

In the thus obtained copolymer (N-10), the content of a DMA-derived repeating unit was 85% by mass; the content of a GLBT-derived repeating unit was 2.5% by mass; and the content of an SPEGM-derived repeating unit was 12.5% by mass.

Further, the thus obtained copolymer (N-10) had a weight-average molecular weight of 484,000, a number-average molecular weight of 122,000, and a molecular weight distribution of 4.0.

Synthesis Example 11

Synthesis of Copolymer (N-11)

In a flask, 8.5 g of DMA, 0.25 g of GLBT, 1.0 g of LPEGM, 0.25 g of 2-ethylhexyl acrylate (manufactured by Tokyo Chemical Industry Co., Ltd.; hereinafter, referred to as "EHA"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature.

To the thus obtained solution, 12.5 g of methyl isobutyl ketone (manufactured by Wako Pure Chemical Industries, Ltd.; hereinafter, referred to as "MIBK") and 87.5 g of acetone (manufactured by Wako Pure Chemical Industries, Ltd.) were added, and this mixture was stirred and then left to stand at room temperature for 1 hour, thereby separating the resultant into a lower layer containing a copolymer (N-11) and an upper layer. After removing the upper layer, an upper layer was once again removed by the same operation. Subsequently, 75 g of MIBK was added to the remaining copolymer (N-11) layer, and the resulting solution was homogenized by stirring. Then, 75 g of diisopropyl ether (manufactured by Tokyo Chemical Industry Co., Ltd.; hereinafter, referred to as "DIPE") was further added thereto, and this solution was stirred to precipitate the copolymer (N-11). Thereafter, the solution was filtered, and the filtration residue was vacuum-dried at 40° C. for 8 hours, whereby the copolymer (N-11) was obtained.

In the thus obtained copolymer (N-11), the content of a DMA-derived repeating unit was 85% by mass; the content of a GLBT-derived repeating unit was 2.5% by mass; the content of an LPEGM-derived repeating unit was 10% by mass; and the content of an EHA-derived repeating unit was 2.5% by mass.

Further, the thus obtained copolymer (N-11) had a weight-average molecular weight of 513,000, a number-average molecular weight of 145,000, and a molecular weight distribution of 3.5.

Synthesis Example 12

Synthesis of Copolymer (N-12)

In a flask, 8.5 g of DMA, 0.25 g of GLBT, 1.0 g of LPEGM, 0.25 g of lauryl methacrylate (LIGHT ESTER L (manufactured by Kyoeisha Chemical Co., Ltd.); hereinafter, referred to as "LMA"), 0.1 g of AIBN, and 90 g of TBA were added and mixed together. Then, nitrogen was blown into the resulting mixture, and the mixture was heated to 60°

C. and allowed to polymerize for 4 hours, after which the resultant was cooled to room temperature.

Subsequently, 100 g of MIBK was added to the thus obtained solution, and this solution was homogenized by stirring. The resulting polymerization solution thus diluted with MIBK was added dropwise with stirring to a vessel containing 1,100 g of DIPE so as to precipitate a copolymer (N-12). Thereafter, the resultant was filtered, and the filtration residue was vacuum-dried at 40° C. for 8 hours, whereby the copolymer (N-12) was obtained.

In the thus obtained copolymer (N-12), the content of a DMA-derived repeating unit was 85% by mass; the content of a GLBT-derived repeating unit was 2.5% by mass; the content of an LPEGM-derived repeating unit was 10% by mass; and the content of an LMA-derived repeating unit was 2.5% by mass.

Further, the thus obtained copolymer (N-12) had a weight-average molecular weight of 465,000, a number-average molecular weight of 119,000, and a molecular weight distribution of 3.9.

Synthesis Example 13

Synthesis of Copolymer (N-13)

In a flask, 8.5 g of DMA, 0.25 g of GLBT, 1.0 g of LPEGM, 0.25 g of dodecylacrylamide (manufactured by Tokyo Chemical Industry Co., Ltd.; hereinafter, referred to as "DDAA"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature.

To the thus obtained solution, 12.5 g of MIBK and 87.5 g of acetone were added, and this mixture was stirred and then left to stand at room temperature for 1 hour, thereby separating the resultant into a lower layer containing a copolymer (N-13) and an upper layer. After removing the upper layer, an upper layer was once again removed by the same operation. Subsequently, 75 g of MIBK was added to the remaining copolymer (N-13) layer, and the resulting solution was homogenized by stirring. Then, 75 g of DIPE was further added thereto, and this solution was stirred to precipitate the copolymer (N-13). Thereafter, the solution was filtered, and the filtration residue was vacuum-dried at 40° C. for 8 hours, whereby the copolymer (N-13) was obtained.

In the thus obtained copolymer (N-13), the content of a DMA-derived repeating unit was 85% by mass; the content of a GLBT-derived repeating unit was 2.5% by mass; the content of an LPEGM-derived repeating unit was 10° by mass; and the content of a DDAA-derived repeating unit was 2.5° by mass.

Further, the thus obtained copolymer (N-13) had a weight-average molecular weight of 497,000, a number-average molecular weight of 130,000, and a molecular weight distribution of 3.8.

Synthesis Example 14

Synthesis of Copolymer (N-14)

In a flask, 8.5 g of DMA, 0.25 g of GLBT, 1.0 g of LPEGM, 0.25 g of silicone methacrylate represented by the below-described Formula (X) (manufactured by Tokyo Chemical Industry Co., Ltd.; hereinafter, referred to as "SiMA"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature.

To the thus obtained solution, 12.5 g of MIBK and 87.5 g of acetone were added, and this mixture was stirred and then left to stand at room temperature for 1 hour, thereby separating the resultant into a lower layer containing a copolymer (N-14) and an upper layer. After removing the upper layer, an upper layer was once again removed by the same operation. Subsequently, 75 g of MIBK was added to the remaining copolymer (N-14) layer, and the resulting solution was homogenized by stirring. Then, 75 g of DIPE was further added thereto, and this solution was stirred to precipitate the copolymer (N-14). Thereafter, the solution was filtered, and the filtration residue was vacuum-dried at 40° C. for 8 hours, whereby the copolymer (N-14) was obtained.

In the thus obtained copolymer (N-14), the content of a DMA-derived repeating unit was 85% by mass; the content of a GLBT-derived repeating unit was 2.5% by mass; the content of an LPEGM-derived repeating unit was 10% by mass; and the content of an SiMA-derived repeating unit was 2.5% by mass.

Further, the thus obtained copolymer (N-14) had a weight-average molecular weight of 462,000, a number-average molecular weight of 108,000, and a molecular weight distribution of 4.3.

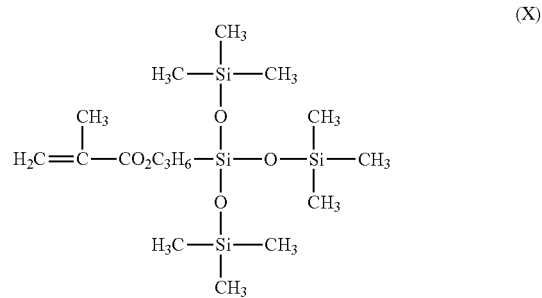

Synthesis Example 15

Synthesis of Copolymer (N-15)

In a flask, 8.5 g of DMA, 0.25 g of GLBT, 1.0 g of LPEGM, 0.25 g of silicone methacrylate (SILAPLANE FM-0711 (manufactured by JNC Corporation); hereinafter, referred to as "DMSMA"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature.

To the thus obtained solution, 12.5 g of MIBK and 87.5 g of acetone were added, and this mixture was stirred and then left to stand at room temperature for 1 hour, thereby separating the resultant into a lower layer containing a copolymer (N-15) and an upper layer. After removing the upper layer, an upper layer was once again removed by the same operation. Subsequently, 75 g of MIBK was added to the remaining copolymer (N-15) layer, and the resulting solution was homogenized by stirring. Then, 75 g of DIPE was further added thereto, and this solution was stirred to precipitate the copolymer (N-15). Thereafter, the solution was filtered, and the filtration residue was vacuum-dried at 40° C. for 8 hours, whereby the copolymer (N-15) was obtained.

In the thus obtained copolymer (N-15), the content of a DMA-derived repeating unit was 85% by mass; the content of a GLBT-derived repeating unit was 2.5° by mass; the content of an LPEGM-derived repeating unit was 10° by mass; and the content of a DMSMA-derived repeating unit was 2.5° by mass.

Further, the thus obtained copolymer (N-15) had a weight-average molecular weight of 497,000, a number-average molecular weight of 103,000, and a molecular weight distribution of 4.8.

Synthesis Example 16

Synthesis of Copolymer (N-16)

In a flask, 7.75 g of DMA, 0.5 g of GLBT, 1.0 g of LPEGM, 0.25 g of DDAA, 0.5 g of diacetone acrylamide (manufactured by Nippon Kasei Chemical Co., Ltd.; hereinafter, referred to as "DAAM"), 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature.

To the thus obtained solution, 12.5 g of MIBK and 87.5 g of acetone were added, and this mixture was stirred and then left to stand at room temperature for 1 hour, thereby separating the resultant into a lower layer containing a copolymer (N-16) and an upper layer. After removing the upper layer, an upper layer was once again removed by the same operation. Subsequently, 75 g of MIBK was added to the remaining copolymer (N-16) layer, and the resulting solution was homogenized by stirring. Then, 75 g of DIPE was further added thereto, and this solution was stirred to precipitate the copolymer (N-16). Thereafter, the solution was filtered, and the filtration residue was vacuum-dried at 40° C. for 8 hours, whereby the copolymer (N-16) was obtained.

In the thus obtained copolymer (N-16), the content of a DMA-derived repeating unit was 77.5% by mass; the content of a GLBT-derived repeating unit was 5% by mass; the content of an LPEGM-derived repeating unit was 10% by mass; the content of a DDAA-derived repeating unit was 2.5% by mass; and the content of a DAAM-derived repeating unit was 5% by mass.

Further, the thus obtained copolymer (N-16) had a weight-average molecular weight of 408,000, a number-average molecular weight of 106,000, and a molecular weight distribution of 3.8.

Reference Example 1

Synthesis of Copolymer (N-17)

In a flask, 8.5 g of DMA, 0.25 g of GLBT, 1.25 g of EHA, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. Thereafter, the thus obtained solution was dialyzed with pure water, whereby an aqueous solution of a copolymer (N-17) was obtained.

In the thus obtained copolymer (N-17), the content of a DMA-derived repeating unit was 85% by mass; the content of a GLBT-derived repeating unit was 2.5% by mass; and the content of an EHA-derived repeating unit was 12.5% by mass.

Further, the thus obtained copolymer (N-17) had a weight-average molecular weight of 354,000, a number-average molecular weight of 83,000, and a molecular weight distribution of 4.3.

Reference Example 2

Synthesis of Copolymer (N-18)

In a flask, 8.5 g of DMA, 0.25 g of GLBT, 1.25 g of LMA, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. The thus obtained solution was re-precipitated with pure water and then dried, whereby a copolymer (N-18) was obtained.

In the thus obtained copolymer (N-18), the content of a DMA-derived repeating unit was 85° by mass; the content of a GLBT-derived repeating unit was 2.5° by mass; and the content of an LMA-derived repeating unit was 12.5° by mass.

Further, the thus obtained copolymer (N-18) had a weight-average molecular weight of 438,000, a number-average molecular weight of 101,000, and a molecular weight distribution of 4.3.

Reference Example 3

Synthesis of Copolymer (N-19)

In a flask, 8.5 g of DMA, 0.25 g of GLBT, 1.25 g of DDAA, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. The thus obtained solution was re-precipitated with pure water and then dried, whereby a copolymer (N-19) was obtained.

In the thus obtained copolymer (N-19), the content of a DMA-derived repeating unit was 85% by mass; the content of a GLBT-derived repeating unit was 2.5% by mass; and the content of a DDAA-derived repeating unit was 12.5% by mass.

Further, the thus obtained copolymer (N-19) had a weight-average molecular weight of 406,000, a number-average molecular weight of 81,000, and a molecular weight distribution of 5.0.

Reference Example 4

Synthesis of Copolymer (N-20)

In a flask, 8.5 g of DMA, 0.25 g of GLBT, 1.25 g of SiMA, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. The thus obtained solution was re-precipitated with pure water and then dried, whereby a copolymer (N-20) was obtained.

In the thus obtained copolymer (N-20), the content of a DMA-derived repeating unit was 85% by mass; the content of a GLBT-derived repeating unit was 2.5% by mass; and the content of an SiMA-derived repeating unit was 12.5% by mass.

Further, the thus obtained copolymer (N-20) had a weight-average molecular weight of 360,000, a number-average molecular weight of 95,000, and a molecular weight distribution of 3.8.

Reference Example 5

Synthesis of Copolymer (N-21)

In a flask, 8.5 g of DMA, 0.25 g of GLBT, 1.25 g of DMSMA, 0.1 g of AIBN, 27 g of pure water, and 63 g of acetonitrile were added and mixed together. Then, nitrogen was blown into the resulting mixture, and the mixture was heated to 60° C. and allowed to polymerize for 4 hours, after which the resultant was cooled to room temperature. The thus obtained solution was re-precipitated with pure water and then dried, whereby a copolymer (N-21) was obtained.

In the thus obtained copolymer (N-21), the content of a DMA-derived repeating unit was 85% by mass; the content of a GLBT-derived repeating unit was 2.5% by mass; and the content of a DMSMA-derived repeating unit was 12.5% by mass.

Further, the copolymer (N-21) had a weight-average molecular weight of 325,000, a number-average molecular weight of 77,000, and a molecular weight distribution of 4.2.

The copolymers (N-1) to (N-21) obtained in Synthesis Examples and Reference Examples were each mixed with purified water at 25° C. such that the resultants each had a concentration of the respective copolymer of 0.5% by mass. The copolymers (N-1) to (N-17), (N-19) and (N-20) were dissolved in the purified water.

TABLE 1

| | | Synthesis Example 1 N-1 | Synthesis Example 2 N-2 | Synthesis Example 3 N-3 | Synthesis Example 4 N-4 | Synthesis Example 5 N-5 | Synthesis Example 6 N-6 | Synthesis Example 7 N-7 | Synthesis Example 8 N-8 | Synthesis Example 9 N-9 | Synthesis Example 10 N-10 |
|---|---|---|---|---|---|---|---|---|---|---|---|
| A | MPEGM | 85 | | | | | | | | | |
| | ACM | | 85 | | | | | | | | |
| | DMA | | | 85 | | 85 | 85 | 85 | | | 85 |
| | NVP | | | | 85 | | | | | | |
| | MPC | | | | | 2.5 | | | 87.5 | | |
| | GLBT | 2.5 | 2.5 | 2.5 | 2.5 | | | | | 87.5 | 2.5 |
| | AA | | | | | | 2.5 | | | | |
| | QA | | | | | | | 2.5 | | | |
| B | LPEGM | 12.5 | 12.5 | 12.5 | 12.5 | 12.5 | 12.5 | 12.5 | 12.5 | 12.5 | |
| | SPEGM | | | | | | | | | | 12.5 |
| C | EHA | | | | | | | | | | |
| | LMA | | | | | | | | | | |
| | DDAA | | | | | | | | | | |
| | SiMA | | | | | | | | | | |
| | DMSMA | | | | | | | | | | |
| D | DAAM | | | | | | | | | | |
| Mw | | 235,000 | 455,000 | 499,000 | 208,000 | 494,000 | 436,000 | 549,000 | 153,000 | 197,000 | 484,000 |
| Mw/Mn | | 4.1 | 3.3 | 4.0 | 4.8 | 3.2 | 4.2 | 3.2 | 3.9 | 4.5 | 4.0 |
| Solubility in water (0.5% by mass) | | ◯ | ◯ | ◯ | ◯ | ◯ | ◯ | ◯ | ◯ | ◯ | ◯ |

TABLE 2

| | | Synthesis Example 11 N-11 | Synthesis Example 12 N-12 | Synthesis Example 13 N-13 | Synthesis Example 14 N-14 | Synthesis Example 15 N-15 | Synthesis Example 16 N-16 |
|---|---|---|---|---|---|---|---|
| A | MPEGM | | | | | | |
| | ACM | | | | | | |
| | DMA | 85 | 85 | 85 | 85 | 85 | 77.5 |
| | NVP | | | | | | |
| | MPC | | | | | | |
| | GLBT | 2.5 | 2.5 | 2.5 | 2.5 | 2.5 | 5 |
| | AA | | | | | | |
| | QA | | | | | | |
| B | LPEGM | 10 | 10 | 10 | 10 | 10 | 10 |
| | SPEGM | | | | | | |
| C | EHA | 2.5 | | | | | |
| | LMA | | 2.5 | | | | |
| | DDAA | | | 2.5 | | | 2.5 |
| | SiMA | | | | 2.5 | | |
| | DMSMA | | | | | 2.5 | |
| D | DAAM | | | | | | 5 |
| Mw | | 513,000 | 465,000 | 497,000 | 462,000 | 497,000 | 408,000 |
| Mw/Mn | | 3.5 | 3.9 | 3.8 | 4.3 | 4.8 | 3.8 |
| Solubility in water (0.5% by mass) | | ◯ | ◯ | ◯ | ◯ | ◯ | ◯ |

TABLE 2-continued

|   |   | Reference Example 1 N-17 | Reference Example 2 N-18 | Reference Example 3 N-19 | Reference Example 4 N-20 | Reference Example 5 N-21 |
|---|---|---|---|---|---|---|
| A | MPEGM | | | | | |
|   | ACM | | | | | |
|   | DMA | 85 | 85 | 85 | 85 | 85 |
|   | NVP | | | | | |
|   | MPC | | | | | |
|   | GLBT | 2.5 | 2.5 | 2.5 | 2.5 | 2.5 |
|   | AA | | | | | |
|   | QA | | | | | |
| B | LPEGM | | | | | |
|   | SPEGM | | | | | |
| C | EHA | 12.5 | | | | |
|   | LMA | | 12.5 | | | |
|   | DDAA | | | 12.5 | | |
|   | SiMA | | | | 12.5 | |
|   | DMSMA | | | | | 12.5 |
| D | DAAM | | | | | |
|   | Mw | 354,000 | 438,000 | 406,000 | 360,000 | 325,000 |
|   | Mw/Mn | 4.3 | 4.3 | 5.0 | 3.8 | 4.2 |
|   | Solubility in water (0.5% by mass) | ○ | X | ○ | ○ | X |

Example 1-1

A 0.5%-by-mass aqueous solution was prepared using the aqueous solution of the copolymer (N-1) obtained in Synthesis Example 1. A urethane substrate was immersed in this aqueous solution and left to stand at 35° C. for 2 hours. Then, the substrate was washed with pure water three times to remove unadsorbed polymer, whereby a urethane substrate coated with the copolymer (N-1) was obtained.

Examples 1-2 to 1-16 and Comparative Examples 1-1 to 1-3

Urethane substrates coated with the respective copolymers were obtained in the same manner as in Example 1-1, except that the aqueous solutions of the copolymers obtained in Synthesis Examples to 2 to 16 and Reference Examples 1,3 and 4 were each used in place of the aqueous solution of the copolymer (N-1).

Example 1-17

A 0.5%-by-mass aqueous solution was prepared using the copolymer (N-16) obtained in Synthesis Example 16. Further, adipic acid dihydrazide in an amount of 1/10 (by mass) of the copolymer was added to and dissolved in the thus obtained aqueous solution. A urethane substrate was immersed in this aqueous solution and left to stand at 35° C. for 2 hours, after which the urethane substrate was taken out of the aqueous solution and then heat-dried in an oven set at 60° C. for at least 4 hours. Thereafter, the substrate was washed with pure water three times, whereby a urethane substrate cross-linked and coated with the copolymer (N-16) was obtained.

Examples 1-18 to 1-33 and Comparative Examples 1-4 to 1-6

Nylon substrates coated with the respective copolymers were each obtained in the same manner as in Examples 1-1 to 1-16 and Comparative Examples 1-1 to 1-3, except that the urethane substrate was changed to a nylon substrate.

Example 1-34

A nylon substrate cross-linked and coated with the copolymer (N-16) was obtained in the same manner as in Example 1-17, except that the urethane substrate was changed to a nylon substrate.

Test Example 1

Hydrophilicity Test

For the substrates of Examples 1-1 to 1-34 and Comparative Examples 1-1 to 1-6, after wiping off the moisture from the surface of each substrate, a contact angle was measured by a droplet method using a contact angle meter DM-701 (manufactured by Kyowa Interface Science Co., Ltd.). As the droplet, 2 μL of physiological saline was used. The test results are shown in Tables 3 and 4.

In the below-described tests, a substrate not coated with the copolymers obtained in Synthesis Examples and Reference Examples was used as a control.

Test Example 2

Surface Lubricity Test

For each of the substrates of Examples 1-1 to 1-34 and Comparative Examples 1-1 to 1-6, the frictional coefficient was measured using an automatic frictional wear analyzer TS501 (manufactured by Kyowa Interface Science Co., Ltd.).

Physiological saline in an amount of 200 μL was placed on immobilized substrate, and a point contactor was moved thereon at a load of 100 gf and a speed of 8 mm/s over a width of 20 mm. The frictional coefficient was measured for the first reciprocating movement of the point contactor, and the frictional coefficient was also measured in the same manner for each of the second to the fifth reciprocating movements. It is noted here that the frictional coefficient was measured at the same spot on each substrate. The average of the frictional coefficient values measured for the first to the fifth reciprocations was defined as the initial frictional coefficient, and the measurement results are shown in Tables 3 and 4 below.

Test Example 3

Durability Test

On each of the substrates of Examples 1-1 to 1-34 and Comparative Examples 1-1 to 1-6, a point contactor was moved under the same conditions as in Test Example 2. The frictional coefficient was measured for the 101st reciprocating movement of the point contactor, and the frictional coefficient was also measured in the same manner for each of the 102nd to the 105th reciprocating movements, after which the average of the thus measured values (frictional coefficient after 100 reciprocations) was calculated. It is noted here that the frictional coefficient was measured at the same spot on each substrate. The results of Test Example 2 were compared with the thus obtained results of the frictional coefficient after 100 reciprocations, and the durability was evaluated as follows. The test results are shown in Tables 3 and 4.

◯: No change in frictional coefficient was observed.
Δ: The frictional coefficient was increased (but less than the frictional coefficient in the pre-coating state)
×: The frictional coefficient was increased to at least a level substantially the same as the pre-coating state.

TABLE 3

| | | Polymer | Polymer concentration (% by weight) | Cross-linking | Substrate | Initial contact angle (°) | Initial frictional coefficient | Durability after 100 reciprocations |
|---|---|---|---|---|---|---|---|---|
| Control | | — | — | — | urethane | 79 | 0.56 | — |
| Example | 1-1 | N-1 | 0.5 | — | urethane | 22 | 0.09 | Δ |
| | 1-2 | N-2 | 0.5 | — | urethane | 20 | 0.06 | ◯ |
| | 1-3 | N-3 | 0.5 | — | urethane | 17 | 0.07 | ◯ |
| | 1-4 | N-4 | 0.5 | — | urethane | 19 | 0.07 | ◯ |
| | 1-5 | N-5 | 0.5 | — | urethane | 23 | 0.05 | ◯ |
| | 1-6 | N-6 | 0.5 | — | urethane | 21 | 0.06 | ◯ |
| | 1-7 | N-7 | 0.5 | — | urethane | 17 | 0.07 | ◯ |
| | 1-8 | N-8 | 0.5 | — | urethane | 23 | 0.07 | Δ |
| | 1-9 | N-9 | 0.5 | — | urethane | 15 | 0.09 | Δ |
| | 1-10 | N-10 | 0.5 | — | urethane | 18 | 0.07 | ◯ |
| | 1-11 | N-11 | 0.5 | — | urethane | 18 | 0.05 | ◯ |
| | 1-12 | N-12 | 0.5 | — | urethane | 22 | 0.07 | ◯ |
| | 1-13 | N-13 | 0.5 | — | urethane | 21 | 0.03 | ◯ |
| | 1-14 | N-14 | 0.5 | — | urethane | 28 | 0.09 | Δ |
| | 1-15 | N-15 | 0.5 | — | urethane | 16 | 0.05 | ◯ |
| | 1-16 | N-16 | 0.5 | — | urethane | 18 | 0.04 | ◯ |
| | 1-17 | N-16 | 0.5 | ◯ | urethane | 12 | 0.01 | ◯ |
| Comparative | 1-1 | N-17 | 0.5 | — | urethane | 53 | 0.15 | X |
| Example | 1-2 | N-19 | 0.5 | — | urethane | 35 | 0.17 | X |
| | 1-3 | N-20 | 0.5 | — | urethane | 65 | 0.19 | X |

TABLE 4

| | | Polymer | Polymer concentration (wt %) | Cross-linking | Substrate | Initial contact angle (°) | Initial frictional coefficient | Durability after 100 reciprocation |
|---|---|---|---|---|---|---|---|---|
| Control | | — | — | — | nylon | 85 | 0.15 | — |
| Example | 1-18 | N-1 | 0.5 | — | nylon | 24 | 0.05 | Δ |
| | 1-19 | N-2 | 0.5 | — | nylon | 28 | 0.05 | ◯ |
| | 1-20 | N-3 | 0.5 | — | nylon | 26 | 0.04 | Δ |
| | 1-21 | N-4 | 0.5 | — | nylon | 23 | 0.02 | Δ |
| | 1-22 | N-5 | 0.5 | — | nylon | 20 | 0.04 | Δ |
| | 1-23 | N-6 | 0.5 | — | nylon | 26 | 0.05 | Δ |
| | 1-24 | N-7 | 0.5 | — | nylon | 24 | 0.03 | Δ |
| | 1-25 | N-8 | 0.5 | — | nylon | 32 | 0.05 | Δ |
| | 1-26 | N-9 | 0.5 | — | nylon | 26 | 0.06 | Δ |
| | 1-27 | N-10 | 0.5 | — | nylon | 21 | 0.04 | ◯ |
| | 1-28 | N-11 | 0.5 | — | nylon | 28 | 0.05 | ◯ |
| | 1-29 | N-12 | 0.5 | — | nylon | 25 | 0.01 | ◯ |
| | 1-30 | N-13 | 0.5 | — | nylon | 20 | 0.02 | ◯ |
| | 1-31 | N-14 | 0.5 | — | nylon | 32 | 0.02 | Δ |
| | 1-32 | N-15 | 0.5 | — | nylon | 35 | 0.04 | Δ |
| | 1-33 | N-16 | 0.5 | — | nylon | 24 | 0.03 | ◯ |
| | 1-34 | N-16 | 0.5 | ◯ | nylon | 15 | 0.00 | ◯ |
| Comparative | 1-4 | N-17 | 0.5 | — | nylon | 23 | 0.11 | X |
| Example | 1-5 | N-19 | 0.5 | — | nylon | 42 | 0.12 | X |
| | 1-6 | N-20 | 0.5 | — | nylon | 73 | 0.11 | X |

Examples 2-1 to 2-15 and Comparative Examples 2-1 to 2-3

Using each of the copolymers (aqueous solutions) of Synthesis Examples 1 to 15 and Reference Examples 1,3 and 4 along with pure water, compositions of Examples 2-1 to 2-15 and Comparative Examples 2-1 to 2-3 were prepared such that the compositions had the respective polymer concentrations shown in Table 5.

The thus obtained compositions were subjected to the following tests. The test results are shown in Tables 5 and 6. It is noted here that, for the control in Table 5, the results of performing the tests in the same manner, except that pure water was used in place of the composition, are shown.

Test Example 1

Cell Adhesion Test (1)

To wells of a 6-well plate having a polystyrene-made surface, the compositions of Examples 2-1 to 2-15 and Comparative Examples 2-1 to 2-3 shown in Table 5 below were each added in an amount of 2 mL, and the plate was left to stand for 2 hours while being heated at 35° C. Thereafter, the plate was washed with pure water three times to remove unadsorbed polymer.

Then, a liquid culture medium, which contained FBS (fetal bovine serum) containing HeLa cells (human cervical cancer cells) at a concentration of $6.7 \times 10^4$ cells/mL, was added to the wells in an amount of 1.5 mL each, and the cells were cultured for 4 hours under the conditions of 37° C. and 5% $CO_2$.

Subsequently, the culture medium was changed and, after further culturing for 44 hours (37° C., 5% $CO_2$), the state of the cells was observed under an inverted microscope, and the number of the cells was measured using a hemocytometer.

The average value of the adhered cell density was calculated in accordance with the following equation. It is noted here that the evaluation was performed at n=3, and the adhered cell density was evaluated based on the below-described criteria.

Adhered cell density (%)=[(Number of adhered cells)/(Number of cells at confluence)]×100

(Evaluation Criteria)
Ranks of Cell Aggregation
×: The adhered cell density was 40% or higher.
Δ: The adhered cell density was 10% to less than 40%.
○: The adhered cell density was less than 10%.

Test Example 2

Cell Adhesion Test (2)

The adhered cell density was evaluated in the same manner as in Test Example 1, except that HeLa cells were changed to 3T3 cells (mouse fibroblasts). The test results are shown in Table 5.

Test Example 3

Cell Adhesion Test (3)

The adhered cell density was evaluated in the same manner as in Test Example 1, except that HeLa cells were changed to UV-2 cells (mouse endothelial cells). The test results are shown in Table 5.

Test Example 4

Measurement of Amount of Adsorbed Antibody

The compositions of Examples and Comparative Examples were each added to a polystyrene-made 96-well plate in an amount of 1 mL, and the plate was left to stand for 4 hours while being heated at 35° C., after which the plate was washed with pure water three times to remove unadsorbed polymer. Then, the 96-well plate was filled with 1 mL of an aqueous solution of horseradish peroxidase-labeled mouse IgG antibody (AP124P, manufactured by Merck Millipore Corporation) and, after incubating the plate for 1 hour at room temperature, the plate was washed with phosphate-buffered physiological saline (PBS) three times. Thereafter, the antibody was allowed to develop a color using TMB (3,3',5,5'-tetramethylbenzidine)/hydrogen peroxide solution/sulfuric acid, and the absorbance was measured for light having a wavelength of 450 nm. From the thus measured absorbance, the amount of adsorbed antibody was determined by a calibration curve method.

Test Example 5

Cytotoxicity Test (1)

To the wells of a commercially available 48-well plate (manufactured by IWAKI Co., Ltd.) which had been hydrophilized for cell culture, a liquid culture medium (10%-by-volume FBS) containing HeLa cells at a concentration of $2 \times 10^4$ cells/mL was added in an amount of 200 µL each, and the cells were precultured for 12 hours under the conditions of 37° C. and 5% $CO_2$.

Meanwhile, copolymer-containing culture media were prepared such that the culture media each contained 0.10% by mass of the respective copolymers of Examples 2-16 and 2-17 and Comparative Examples of 2-4 and 2-5 shown in Table 6 and had an aqueous copolymer solution content of 10% by mass.

Then, the precultured medium of HeLa cells was changed to each copolymer-containing culture medium prepared above, and the cells were cultured for 24 hours under the conditions of 37° C. and 5% $CO_2$. It is noted here that, for control, culturing was performed in the same manner as described above, except that the aqueous copolymer solution was changed to pure water.

Using the thus cultured cells, the cytotoxicity of each copolymer was verified by MTT assay. The MTT assay was performed using an MTT assay kit (MTT Cell Proliferation Assay Kit 10009365, manufactured by Cayman Chemical Company) in accordance with the accompanying manual. The results are shown in Table 6.

It is noted here that the values shown in Table 6 are relative values taking the value of the control as 100%, and a value of 80% or higher indicates the absence of toxicity, with a lower value indicating a higher toxicity of the copolymer.

Test Example 6

Cytotoxicity Test (2)

The cytotoxicity was verified in the same manner as in Test Example 5, except that HeLa cells were changed to 3T3 cells. The results are shown in Table 6.

Test Example 7

Cytotoxicity Test (3)

The cytotoxicity was verified in the same manner as in Test Example 5, except that HeLa cells were changed to UV-2 cells. The results are shown in Table 6.

Test Example 8

Production of Cell Cluster

The compositions of Examples and Comparative Examples were each added to a U-bottomed 96-well plate in an amount of 180 μL, and the plate was left to stand for 2 hours while being heated at 37° C., after which the plate was washed with PBS three times to remove unadsorbed polymer.

Then, 100 μL of a liquid culture medium (10%-by-volume FBS) containing HT29 cells (human colon cancer cells) at a concentration of $2.5 \times 10^4$ cells/mL was added to the wells. After culturing the inoculated cells for 16 hours under the conditions of 37° C. and 5% $CO_2$, the state of the cells was observed under a light microscope. When the cells adhered to the bottom of a well, a state of the cells being scattered over the entire well was observed. Meanwhile, when the cells did not adhere to the well, the cells aggregated in the center near the U-shaped bottom to form a cell cluster. This test was conducted at n=3, and the rank of cell aggregation was evaluated based on the average value. The cell aggregation was evaluated in accordance with the following criteria.

(Evaluation Criteria)
Ranks of Cell Aggregation
 1: Cells were scattered over the entirety of each well.
 2: Cells tended to aggregate in the center of each well.
 3: Cells aggregated in the center of each well and formed a cell cluster.

TABLE 6

|  |  | Polymer | Polymer concentration (% by weight) | Cytotoxicity (%) | | |
|---|---|---|---|---|---|---|
|  |  |  |  | HeLa | 3T3 | UV♀2 |
| Control |  | — | — | 100 | 100 | 100 |
| Example | 2-16 | N-3 | 0.1 | 91 | 94 | 98 |
|  | 2-17 | N-13 | 0.1 | 85 | 103 | 97 |
| Comparative | 2-4 | N-19 | 0.1 | 77 | 101 | 92 |
| Example | 2-5 | N-20 | 0.1 | 88 | 93 | 95 |

Examples 3-1 to 3-15 and Comparative Examples 3-1 to 3-3

Using each of the copolymers (aqueous solutions) of Synthesis Examples 1 to 15 and Reference Examples 1, 3 and 4 along with pure water, treatment compositions of Examples 3-1 to 3-15 and Comparative Examples 3-1 to 3-3 were prepared such that the treatment compositions had the respective polymer concentrations shown in Table 7.

The thus obtained treatment compositions were subjected to the following tests. The test results are shown in Table 7. It is noted here that, for the control in Table 7, the results of performing the tests in the same manner, except that pure water was used in place of the treatment composition, are shown.

Test Example 1

Evaluation of Hydrophilicity

First, 0.5 mm-thick silicone rubber sheets (SR-50, manufactured by Tigers Polymer Corporation) cut out into a size of 10 mm×5 mm were prepared.

Then, these silicone rubber sheets were immersed in 1 mL of each of the treatment compositions of Examples and

TABLE 5

|  |  | Polymer | Polymer concentration (% by weight) | Adhered cell density (%) | | | Amount of adsorbed antibody (ng) | Cell cluster |
|---|---|---|---|---|---|---|---|---|
|  |  |  |  | HeLa | 3T3 | UV♀2 |  |  |
| Control |  | — | — | X | X | X | 4.19 | 1 |
| Example | 2-1 | N-1 | 0.5 | ○ | Δ | ○ | 0.31 | — |
|  | 2-2 | N-2 | 0.5 | ○ | ○ | ○ | 0.24 | — |
|  | 2-3 | N-3 | 0.5 | ○ | ○ | ○ | 0.28 | 2.3 |
|  | 2-4 | N-4 | 0.5 | ○ | Δ | ○ | 0.26 | — |
|  | 2-5 | N-5 | 0.5 | ○ | ○ | ○ | 0.17 | — |
|  | 2-6 | N-6 | 0.5 | ○ | ○ | ○ | 0.20 | — |
|  | 2-7 | N-7 | 0.5 | ○ | ○ | ○ | 0.31 | — |
|  | 2-8 | N-8 | 0.5 | ○ | ○ | ○ | 0.12 | — |
|  | 2-9 | N-9 | 0.5 | ○ | ○ | ○ | 0.19 | — |
|  | 2-10 | N-10 | 0.5 | ○ | ○ | ○ | 0.23 | — |
|  | 2-11 | N-11 | 0.5 | ○ | ○ | ○ | 0.27 | — |
|  | 2-12 | N-12 | 0.5 | ○ | ○ | ○ | 0.08 | — |
|  | 2-13 | N-13 | 0.5 | ○ | ○ | ○ | 0.14 | 3 |
|  | 2-14 | N-14 | 0.5 | ○ | Δ | ○ | 0.33 | — |
|  | 2-15 | N-15 | 0.5 | ○ | ○ | Δ | 0.19 | — |
| Comparative | 2-1 | N-17 | 0.5 | ○ | Δ | Δ | 0.72 | — |
| Example | 2-2 | N-19 | 0.5 | ○ | Δ | Δ | 0.58 | 1.0 |
|  | 2-3 | N-20 | 0.5 | Δ | Δ | Δ | 1.23 | 1.3 |

Comparative Examples and left to stand for 4 hours while being heated at 35° C., after which the sheets were washed with pure water three times to remove unadsorbed polymer. Subsequently, after wiping off the moisture from the surface of each sheet, the air bubble contact angle (25° C.) was measured by an air bubble method using a contact angle meter DM-701 (manufactured by Kyowa Interface Science Co., Ltd.). The measurement results obtained by the air bubble method indicate the surface hydrophilicity in a wet state, and a higher hydrophilicity yields a large value.

Test Example 2

Measurement of Amount of Adsorbed Antibody

First, 0.5 mm-thick silicone rubber sheets (SR-50, manufactured by Tigers Polymer Corporation) cut out into a size of φ=6 mm were prepared.

These silicone rubber sheets were immersed in 1 mL of each of the treatment compositions of Examples and Comparative Examples and left to stand for 4 hours while being heated at 35° C., after which the sheets were washed with pure water three times to remove unadsorbed polymer. Subsequently, the thus treated silicone rubber sheets were each immersed in 1 mL of an aqueous solution of horseradish peroxidase-labeled mouse IgG antibody (AP124P, manufactured by Merck Millipore Corporation), left to stand for 1 hour at room temperature, and then washed with PBS three times. The thus washed silicone rubber sheets were transferred to the wells of a polystyrene-made 96-well plate, and the antibody was allowed to develop a color using TMB/hydrogen peroxide solution/sulfuric acid. The absorbance was measured for light having a wavelength of 450 nm and, from the thus measured absorbance, the amount of adsorbed antibody was determined by a calibration curve method.

Test Example 3

Blood Feeding Test

The treatment compositions of Examples 3-3 and 3-13 and Comparative Examples 3-2 and 3-3 shown in Table 7 below were each poured into the channel of a PDMS (polydimethylsiloxane) standard chip having a channel of 200 μm in width and 50 μm in height (manufactured by Fluidware Technologies Inc.). The chip was left to stand for 4 hours while being heated at 35° C., and subsequently washed with pure water three times and then with PBS three times to remove unadsorbed polymer.

Thereafter, a blood sample was fed to the channel for 6 minutes at an inlet flow rate of 2 μL/min under a constant pressure, and the amount of the blood sample discharged from the channel outlet during a period of 1 minute immediately after the initiation of the feeding and the amount of the blood sample discharged from the channel outlet during a period between 5 minutes and 6 minutes after the initiation of the feeding were measured.

TABLE 7

| | | Polymer | Polymer concentration (% by weight) | Treatment temperature (° C.) | Treatment time (min) | Air bubble contact angle (°) | Amount of adsorbed antibody (ng) | Flow rate (μL/min) | |
|---|---|---|---|---|---|---|---|---|---|
| | | | | | | | | Immediately after initiation of feeding to 1 minute thereafter | After 5 to 6 minutes |
| Control | | — | — | 35 | 240 | 93 | 3.60 | 2 | 0.6 |
| Example | 3-1 | N-1 | 0.5 | 35 | 240 | 125 | 0.12 | — | — |
| | 3-2 | N-2 | 0.5 | 35 | 240 | 121 | 0.15 | — | — |
| | 3-3 | N-3 | 0.5 | 35 | 240 | 136 | 0.13 | 2 | 2 |
| | 3-4 | N-4 | 0.5 | 35 | 240 | 138 | 0.08 | — | — |
| | 3-5 | N-5 | 0.5 | 35 | 240 | 143 | 0.02 | — | — |
| | 3-6 | N-6 | 0.5 | 35 | 240 | 131 | 0.06 | — | — |
| | 3-7 | N-7 | 0.5 | 35 | 240 | 137 | 0.07 | — | — |
| | 3-8 | N-8 | 0.5 | 35 | 240 | 118 | 0.09 | — | — |
| | 3-9 | N-9 | 0.5 | 35 | 240 | 114 | 0.12 | — | — |
| | 3-10 | N-10 | 0.5 | 35 | 240 | 123 | 0.08 | — | — |
| | 3-11 | N-11 | 0.5 | 35 | 240 | 146 | 0.03 | | |
| | 3-12 | N-12 | 0.5 | 35 | 240 | 134 | 0.05 | | |
| | 3-13 | N-13 | 0.5 | 35 | 240 | 144 | 0.05 | 2 | 2 |
| | 3-14 | N-14 | 0.5 | 35 | 240 | 134 | 0.06 | — | — |
| | 3-15 | N-15 | 0.5 | 35 | 240 | 138 | 0.04 | — | — |
| Comparative | 3-1 | N-17 | 0.5 | 35 | 240 | 100 | 1.20 | — | — |
| Example | 3-2 | N-19 | 0.5 | 35 | 240 | 98 | 0.95 | 2 | 1.2 |
| | 3-3 | N-20 | 0.5 | 35 | 240 | 107 | 0.88 | 2 | 1.4 |

The invention claimed is:

1. An article comprising, on at least a part of a surface thereof, a polymer having repeating units (A) and (B),
   wherein said article is one selected from the group consisting of a medical device, a cell culture equipment, and a silicone substrate;
   (A) is a hydrophilic repeating unit; and
   (B) is a repeating unit which has a polyoxyalkylene group in a side chain whose terminal is an alkyl group having 5 to 30 carbon atoms, an alkanoyl group having 5 to 30 carbon atoms, or an aryl group having 6 to 30 carbon atoms, and
   wherein the article is a silicone substrate which has a microchannel.

2. The article according to claim 1,
   wherein said repeating unit (A) is at least one selected from the group consisting of a repeating unit (A-1) represented by Formula (1), a repeating unit (A-2) represented by Formula (2), a repeating unit (A-3) represented by Formula (3), a repeating unit (A-4) represented by Formula (4), a repeating unit (A-5) represented by Formula (5), a repeating unit (A-6)

represented by Formula (6), an anionic repeating unit (A-7), and a repeating unit (A-8) represented by Formula (8):

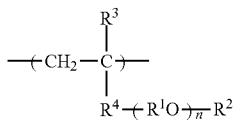

(1)

wherein, $R^1$ represents an alkylene group having 2 to 4 carbon atoms; $R^2$ represents a hydrogen atom or an alkyl group having 1 to 4 carbon atoms; $R^3$ represents a hydrogen atom or a methyl group; $R^4$ represents —O—, *—(C=O)—O—, *—(C=O)—NR$^5$—, *—NR$^5$—(C=O)— where $R^5$ represents a hydrogen atom or an organic group having 1 to 10 carbon atoms, and * represents a position at which the group is bound to a carbon atom bound with $R^3$ in the Formula (1), or a phenylene group; and n represents a value of 2 to 100;

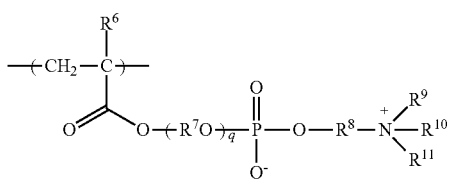

(2)

wherein, $R^6$ represents a hydrogen atom or a methyl group; $R^7$ represents an alkylene group having 2 to 4 carbon atoms; $R^8$ represents an alkylene group having 1 to 10 carbon atoms; $R^9$, $R^{10}$ and $R^{11}$ each independently represent a hydrogen atom or a hydrocarbon group having 1 to 8 carbon atoms; and q represents a value of 1 to 10;

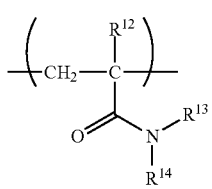

(3)

wherein, $R^{12}$ represents a hydrogen atom or a methyl group; and $R^{13}$ and $R^{14}$ each independently represent a hydrogen atom, an alkyl group having 1 to 6 carbon atoms or hydroxyalkyl group;

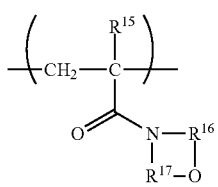

(4)

wherein, $R^{15}$ represents a hydrogen atom or a methyl group; and $R^{16}$ and $R^{17}$ each independently represent an alkylene group having 1 to 3 carbon atoms;

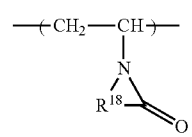

(5)

wherein, $R^{18}$ represents an alkylene group having 1 to 5 carbon atoms;

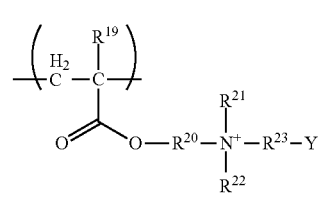

(6)

wherein, Y represents —(C=O)O$^-$, —(O=S=O)O$^-$, —O(O=S=O)O$^-$, —(S=O)O$^-$, —O(S=O)O$^-$, —OP(=O)(OR$^{24}$)O$^-$, —OP(=O)(R$^{24}$)O$^-$, —P(=O)(OR$^{24}$)O$^-$, or —P(=O)(R$^{24}$)O$^-$ where $R^{24}$ represents an alkyl group having 1 to 3 carbon atoms; $R^{19}$ represents a hydrogen atom or a methyl group; $R^{20}$ represents a divalent organic group having 1 to 10 carbon atoms; $R^{21}$ and $R^{22}$ each independently represent a hydrocarbon group having 1 to 10 carbon atoms; and $R^{23}$ represents a divalent organic group having 1 to 10 carbon atoms; and

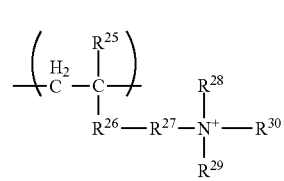

(8)

wherein, $R^{25}$ represents a hydrogen atom or a methyl group; $R^{26}$ represents —O—, *—(C=O)—O—, *—(C=O)—NR$^{31}$—, *—NR$^{31}$—(C=O)— where $R^{31}$ represents a hydrogen atom or an organic group having 1 to 10 carbon atoms, and * represents a position at which the group is bound to a carbon atom bound with $R^{25}$ in the Formula (8), or a phenylene group; $R^{27}$ represents a divalent organic group having 1 to 10 carbon atoms; and $R^{28}$, $R^{29}$ and $R^{30}$ each independently represent a hydrocarbon group having 1 to 10 carbon atoms, wherein the repeating unit (A-8) has a counter ion.

3. The article according to claim 2, wherein in Formula (1), $R^4$ represents *—(C=O)—O— and * represents a position at which the group is bound to a carbon atom bound with $R^3$ in the Formula (1), or a phenylene group.

4. The article according to claim 1, wherein said repeating unit (B) is a repeating unit derived from a monomer having an ethylenically unsaturated bond.

5. The article according to claim 1, wherein said repeating unit (B) is represented by Formula (b2):

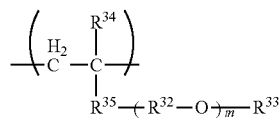
(b2)

wherein, $R^{32}$ represents an alkylene group having 2 to 4 carbon atoms; $R^{33}$ represents an alkyl group having 5 to 30 carbon atoms, an alkanoyl group having 5 to 30 carbon atoms, or an aryl group having 6 to 30 carbon atoms; $R^{34}$ represents a hydrogen atom or a methyl group; $R^{35}$ represents —O—, —(C=O)—O—, —(C=O)—NR$^{36}$—, —NR$^{36}$—(C=O)— where $R^{36}$ represents a hydrogen atom or an organic group having 1 to 10 carbon atoms, and  represents a position at which the group is bound to a carbon atom bound with $R^{34}$ in the Formula (b2), or a phenylene group; and m represents a value of 2 to 100.

6. The article according to claim 1, wherein said polymer further comprises at least one repeating unit (C) selected from the group consisting of a repeating unit (C-1) represented by Formula (c1) and a repeating unit (C-2) having a group represented by Formula (c2) at a side chain terminal:

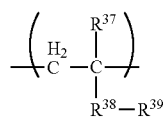
(c1)

wherein, $R^{37}$ represents a hydrogen atom or a methyl group; $R^{38}$ represents —O—, *—(C=O)—O—, *—(C=O)—NR$^{40}$—, *—NR$^{40}$—(C=O)— where $R^{40}$ represents a hydrogen atom or an organic group having 1 to 10 carbon atoms, and * represents a position at which the group is bound to a carbon atom bound with $R^{37}$ in the Formula (c1), or a phenylene group; and $R^{39}$ represents a hydrocarbon group having 4 to 30 carbon atoms; and

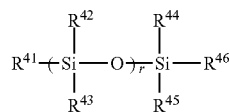
(c2)

wherein, $R^{41}$ represents a divalent organic group having 1 to 10 carbon atoms; $R^{42}$ and $R^{43}$ each independently represent an organic group having 1 to 10 carbon atoms; $R^{44}$, $R^{45}$ and $R^{46}$ each independently represent —OSi(R$^{49}$)$_3$ where each $R^{49}$ independently represents a hydrogen atom or an organic group having 1 to 8 carbon atoms, or an organic group having 1 to 10 carbon atoms; and r represents a value of 0 to 200.

7. The article according to claim 1, wherein said polymer is soluble in water.

8. A method of producing an article selected from the group consisting of a medical device, a cell culture equipment and a silicone substrate, said method comprising arranging a polymer having repeating units (A) and (B) on at least a part of a surface of the article, wherein (A) is a hydrophilic repeating unit; and (B) is a repeating unit which has a polyoxyalkylene group in a side chain whose terminal is an alkyl group having 5 to 30 carbon atoms, an alkanoyl group having 5 to 30 carbon atoms, or an aryl group having 6 to 30 carbon atoms, wherein the article is a silicone substrate which has a microchannel.

9. The method according to claim 8, wherein (A) is a hydrophilic repeating unit; and (B) is a repeating unit which has a polyoxyalkylene group in a side chain whose terminal is an alkyl group having 5 to 30 carbon atoms, or an alkanoyl group having 5 to 30 carbon atoms wherein said repeating unit (A) is at least one selected from the group consisting of a repeating unit (A-1) represented by Formula (1), a repeating unit (A-2) represented by Formula (2), a repeating unit (A-3) represented by Formula (3), a repeating unit (A-4) represented by Formula (4), a repeating unit (A-5) represented by Formula (5), a repeating unit (A-6) represented by Formula (6), an anionic repeating unit (A-7), and a repeating unit (A-8) represented by Formula (8):

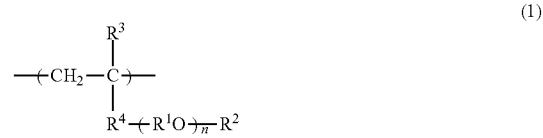
(1)

wherein, $R^1$ represents an alkylene group having 2 to 4 carbon atoms; $R^2$ represents a hydrogen atom or an alkyl group having 1 to 4 carbon atoms; $R^3$ represents a hydrogen atom or a methyl group; $R^4$ represents —O—, *—(C=O)—O—, *—(C=O)—NR$^5$—, *—NR$^5$—(C=O)— where $R^5$ represents a hydrogen atom or an organic group having 1 to 10 carbon atoms, and * represents a position at which the group is bound to a carbon atom bound with $R^3$ in the Formula (1), or a phenylene group; and n represents a value of 2 to 100;

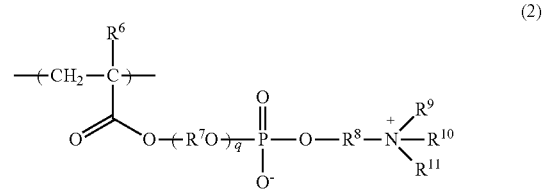
(2)

wherein, $R^6$ represents a hydrogen atom or a methyl group; $R^7$ represents an alkylene group having 2 to 4 carbon atoms; $R^8$ represents an alkylene group having 1 to 10 carbon atoms; $R^9$, $R^{10}$ and $R^{11}$ each independently represent a hydrogen atom or a hydrocarbon group having 1 to 8 carbon atoms; and q represents a value of 1 to 10;

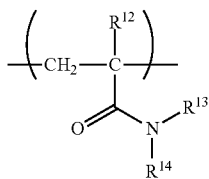
(3)

wherein, $R^{12}$ represents a hydrogen atom or a methyl group; and $R^{13}$ and $R^{14}$ each independently represent a hydrogen atom, an alkyl group having 1 to 6 carbon atoms or hydroxyalkyl group;

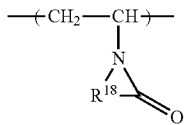
(4)

wherein, $R^{15}$ represents a hydrogen atom or a methyl group; and $R^{16}$ and $R^{17}$ each independently represent an alkylene group having 1 to 3 carbon atoms;

—(CH$_2$—CH)— (5)

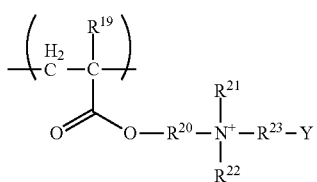

wherein, $R^{18}$ represents an alkylene group having 1 to 5 carbon atoms;

(6)

wherein, Y represents —(C=O)O⁻, —(O=S=O)O⁻, —O(O=S=O)O⁻, —(S=O)O⁻, —O(S=O)O⁻, —OP(=O)(OR²⁴)O⁻, —OP(=O)(R²⁴)O⁻, —P(=O)(OR²⁴)O⁻, or -P(=O)(R²⁴)O⁻ where $R^{24}$ represents an alkyl group having 1 to 3 carbon atoms; $R^{19}$ represents a hydrogen atom or a methyl group; $R^{20}$ represents a divalent organic group having 1 to 10 carbon atoms; $R^{21}$ and $R^{22}$ each independently represent a hydrocarbon group having 1 to 10 carbon atoms; and $R^{23}$ represents a divalent organic group having 1 to 10 carbon atoms; and

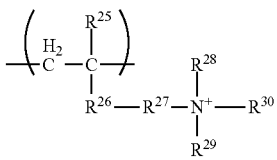
(8)

wherein, $R^{25}$ represents a hydrogen atom or a methyl group; $R^{26}$ represents —O—, *—(C=O)—O—, *—(C=O)—NR³¹—, *—NR³¹—(C=O)— where $R^{31}$ represents a hydrogen atom or an organic group having 1 to 10 carbon atoms, and * represents a position at which the group is bound to a carbon atom bound with $R^{25}$ in the Formula (8), or a phenylene group; $R^{27}$ represents a divalent organic group having 1 to 10 carbon atoms; and $R^{28}$, $R^{29}$ and $R^{30}$ each independently represent a hydrocarbon group having 1 to 10 carbon atoms, wherein the repeating unit (A-8) has a counter ion.

10. The method according to claim 9, wherein in Formula (1), $R^4$ represents *—(C=O)—O— and * represents a position at which the group is bound to a carbon atom bound with $R^3$ in the Formula (1), or a phenylene group.

* * * * *